United States Patent
Van Dijl et al.

(10) Patent No.: US 9,944,694 B2
(45) Date of Patent: Apr. 17, 2018

(54) **ANTIBODIES AGAINST *STAPHYLOCOCCUS AUREUS* AND USES THEROF**

(71) Applicants: RIJKSUNIVERSITEIT GRONINGEN, Groningen (NL); ACADEMISCH ZIEKENHUIS GRONINGEN, Groningen (NL)

(72) Inventors: Jan Maarten Van Dijl, Groningen (NL); Girbe Buist, Groningen (NL); Hendrik Petrus Jozef Bonarius, Groningen (NL); Neeltje Margaretha Kooi, Groningen (NL); Goffe Sytse Elsinga, De Meern (NL); Herman Groen, Groningen (NL)

(73) Assignees: Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 0 days.

(21) Appl. No.: 15/103,586

(22) PCT Filed: Dec. 12, 2014

(86) PCT No.: PCT/NL2014/050857
§ 371 (c)(1),
(2) Date: Jun. 10, 2016

(87) PCT Pub. No.: WO2015/088346
PCT Pub. Date: Jun. 18, 2015

(65) Prior Publication Data
US 2017/0002063 A1    Jan. 5, 2017

(30) Foreign Application Priority Data
Dec. 13, 2013 (EP) ..................................... 13197211

(51) Int. Cl.
C07K 16/12 (2006.01)
G01N 33/569 (2006.01)
A61K 39/00 (2006.01)

(52) U.S. Cl.
CPC ... *C07K 16/1271* (2013.01); *G01N 33/56938* (2013.01); *A61K 2039/505* (2013.01); *A61K 2039/507* (2013.01); *C07K 2317/21* (2013.01); *C07K 2317/33* (2013.01); *C07K 2317/51* (2013.01); *C07K 2317/515* (2013.01); *C07K 2317/565* (2013.01); *C07K 2317/70* (2013.01); *C07K 2317/94* (2013.01); *G01N 2469/10* (2013.01)

(58) Field of Classification Search
None
See application file for complete search history.

(56) References Cited

FOREIGN PATENT DOCUMENTS

| WO | 2007141274 A2 | 12/2007 | |
|---|---|---|---|
| WO | 2010133600 A1 | 11/2010 | |
| WO | 20130417074 A1 | 3/2013 | |
| WO | WO 2013041707 A1 * | 3/2013 | ......... C07K 16/1271 |

OTHER PUBLICATIONS

Sela-Culang et al. 2013 (The structural basis of antibody-antigen recognition; Frontiers in Immunology 4(302):1-13).*
Greenspan et al. 1999 (Defining epitopes: It's not as easy as it seems; Nature Biotechnology, 17:936-937).*
International Search Report from corresponding PCT Application No. PCT/NL2014/050857 dated Mar. 15, 2015.
Kijanka, et al., "Rapid OpticalImaging of Human Breast Tumour Xenograts Using Anti-HER2 VHHs Site-Directly. Conjugated to IRDye 800CW for Image-Guided Surgery", Eur J. Nucl Med Mol Imaging, May 17, 2013, pp. 1718-1729, v. 40, published online.
Lorenz, et al., "Functional Antibodies Targeting IsaA of *Staphylococcus aureus* Augment Host Immune Response and Open New Perspectives for Antibacterial Therapy" Antimicrobial Agents and Chemotherrapt, Jan. 2011, pp. 165-173, v. 55, No. 1, Germany.
Sanne Van Den Berg, et al., "A Human Monoclonal Antibody Targeting the Conserved Staphylococcal antigen IsaaA Protects Mice Against *Staphylococcus aureus* Bacteremia", International Journal of Medical Microbiology, 2015, pp. 55-64, v. 305, No. 1 The Netherlands.
Smith, et al., "Rapid Generation of Fully Human Monoclonal Antibodies Specific to a Vaccinating Antigen", Nature Protocols, pp. 372-384, v. 4, No. 3, published online.
Tiller, et al. "Efficient Generation of Monoclonal Antibodies from Single Human B Cells by Single Cell RT-PCR and Expression Vector Cloning", journal of Immunological Methods, Oct. 31, 2007, pp. 112-124, vol. 329, No. 1-2, Amsterdam, Netherlands.
Van Oosten, et al., "Real-time in vivo Imaging of Invasive- and Biomaterial-associated Bacterial Infections Using Flourescently Labelled Vancomycin", Nature Communications, Oct. 15, 2013, vol. 4.

* cited by examiner

*Primary Examiner* — Mary Maille Lyons
(74) *Attorney, Agent, or Firm* — McDermott Will & Emery, LLP

(57) ABSTRACT

The invention relates to the field of immunology and vaccine development. In particular, it relates to antibodies and fragments thereof against *Staphylococcus aureus* and to therapeutic and diagnostic uses thereof. Provided is an isolated antibody or a functional fragment thereof, which binds to an epitope of the Immunodominant Staphylococcal antigen A (IsaA), wherein said antibody comprises at least four Isa A epitope-binding CDR sequences selected from the group consisting of SEQ ID NO: 1; SEQ ID NO: 2; SEQ ID NO: 3; SEQ ID NO: 4; SEQ ID NO: 5; SEQ ID NO: 6, and functional equivalents thereof having an amino acid sequence that is at least 85% identical to an amino acid sequence of SEQ ID NO: 1-6.

16 Claims, 18 Drawing Sheets

Heavy

Figure 2A:
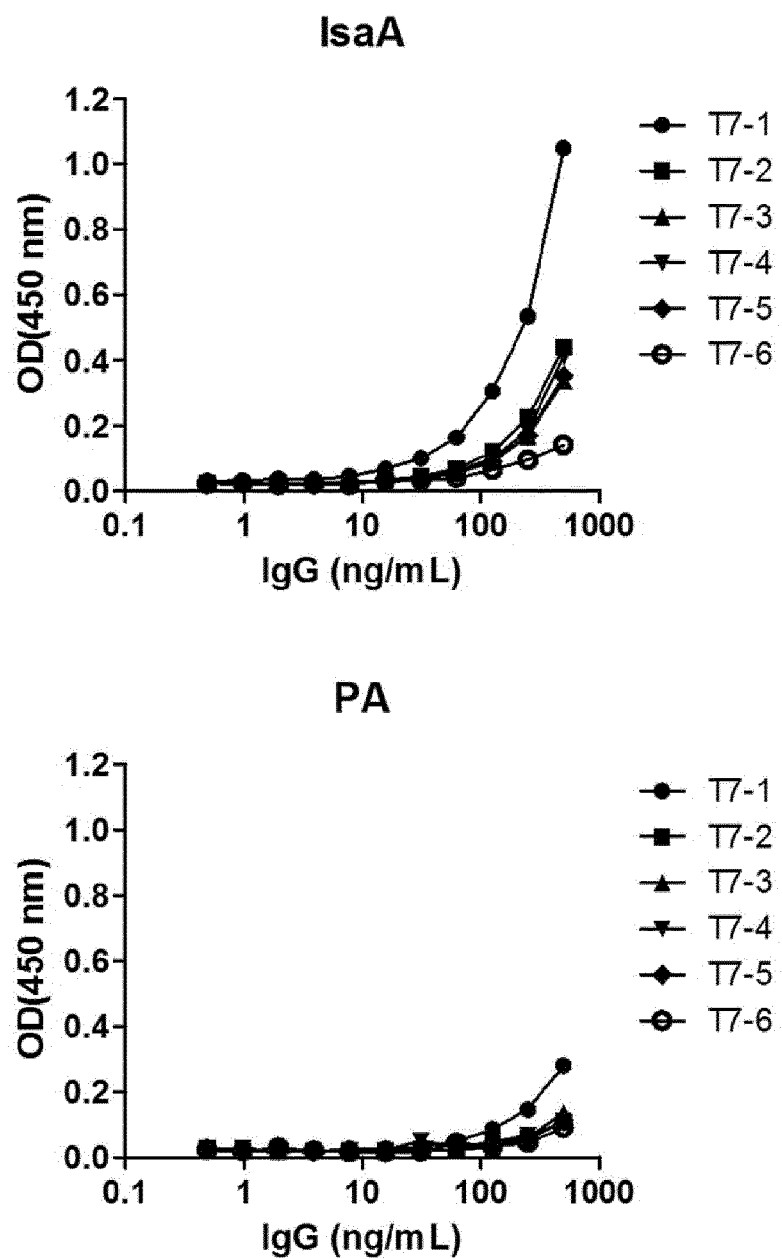

```
                    FR1                    CDR1                  FR2                  CDR2
                   (1-26)                 (27-38)              (39-55)               (56-65)
         1           10          20           30          40          50          60
         :....|....|....|....|....|.. ....|....|....| ....|....|....| ....|....|
1D9      EVQLVESGG.GLVQPGRSLRLSCAAS GFSF.....TNYA   MHWVRQAPGKGLEWVSG ISWN..SGSI
M99651 IGHV3-9*01  EVQLVESGG.GLVQPGRSLRLSCAAS GFTF.....DDYA   MHWVRQAPGKGLEWVSG ISWN..SGSI
                                            S           TN

FR3                                    CDR3              FR4
                   (66-104)                              (105-119)         (120-130)
         70          80          90          100         110         120         130
         :....|....|....|....|....|....|....|....| ....|....|....| ....|....|
         LYADSVK.GRFTISRDNAKDSLYLQMNSLRVEDTAFYYC   AKGMAAAGNTDRFDY WGQGTLVTVSS
         GYADSVK.GRFTISRDNAKNSLYLQMNSLRAEDTALYYC   AKD
         L         D       V  F                   G
```

FIG. 1

Light

```
                   FR1                      CDR1              FR2                CDR2
                  (1-26)                   (27-38)          (39-55)             (56-65)
         1        10        20          30        40         50          60
         |........|.........|...........|.........|..........|...........|.........
1D9 kappa   ..SMTQSPFSLSLSPGERATLSCRAS QSVS......SSY LAWYQQKPGQAPRLLIY GA.........S
X12686 IGKV3-20*01 EIVLTQSPGTLSLSPGERATLSCRAS QSVS......SSY LAWYQQKPGQAPRLLIY GA.........S
                   SM      FS FR3                              CDR3         FR4
                 (66-104)                         (105-113)   (114-123)
         70       80        90        100          110          120
         |........|.........|.........|............|...........|.....
         SRATGIP.DRFSGSG...SGTDFTLTISRLDPEDFAVYYC QQYGGSPIT FGQGTRLEIK
         SRATGIP.DRFSGSG...SGTDFTLTISRLEPEDFAVYYC QQYGSSP
                                      D                 G
```

FIG. 1, Cont'd

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: heavy chain CDR1

<400> SEQUENCE: 1

Gly Phe Ser Phe Thr Asn Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: heavy chain CDR2

<400> SEQUENCE: 2

Ile Ser Trp Asn Ser Gly Ser Ile
```

```
<210> SEQ ID NO 3
<211> LENGTH: 15
<212> TYPE: PRT
<213> ORGANISM: Artificial Sequence
<220> FEATURE:
<223> OTHER INFORMATION: heavy chain CDR3

<400> SEQUENCE: 3

Ala Lys Gly Met Ala Ala Ala Gly Asn Thr Asp Arg Phe Asp Tyr
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: light chain CDR1

<400> SEQUENCE: 4

Gln Ser Val Ser Ser Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: light chain CDR2

<400> SEQUENCE: 5

Gly Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: light chain CDR3

<400> SEQUENCE: 6

Gln Gln Tyr Gly Gly Ser Pro Ile Thr
1               5

<210> SEQ ID NO 7
<211> LENGTH: 21
<212> TYPE: DNA
<213> ORGANISM: Artificial Sequence
<220> FEATURE:
<223> OTHER INFORMATION: Heavy chain CDR1

<400> SEQUENCE: 7
ttcagcttta ctaattatgc c                                          21

<210> SEQ ID NO 8
<211> LENGTH: 24
<212> TYPE: DNA
<213> ORGANISM: Artificial Sequence
<220> FEATURE:
<223> OTHER INFORMATION: Heavy chain CDR2

<400> SEQUENCE: 8
attagttgga atagtggtag cata                                       24

<210> SEQ ID NO 9
```

```
<211> LENGTH: 45
<212> TYPE: DNA
<213> ORGANISM: Artificial Sequence
<220> FEATURE:
<223> OTHER INFORMATION: Heavy chain CDR3

<400> SEQUENCE: 9
gcaaaaggaa tggcagcagc tgggaacact gaccgttttg actac                              45

<210> SEQ ID NO 10
<211> LENGTH: 21
<212> TYPE: DNA
<213> ORGANISM: Artificial Sequence
<220> FEATURE:
<223> OTHER INFORMATION: Light chain CDR1

<400> SEQUENCE: 10
cagagtgtta gcagcagcta c                                                       21

<210> SEQ ID NO 11
<211> LENGTH: 9
<212> TYPE: DNA
<213> ORGANISM: Artificial Sequence
<220> FEATURE:
<223> OTHER INFORMATION: Light chain CDR2

<400> SEQUENCE: 11 ggtgcatcc                                                                      9

<210> SEQ ID NO 12
<211> LENGTH: 27
<212> TYPE: DNA
<213> ORGANISM: Artificial Sequence
<220> FEATURE:
<223> OTHER INFORMATION: Light chain CDR3

<400> SEQUENCE: 12
cagcaatatg gtggctcacc gatcacc                                                 27

<210> SEQ ID NO 13
<211> LENGTH: 111
<212> TYPE: PRT
<213> ORGANISM: Artificial Sequence
<220> FEATURE:
<223> OTHER INFORMATION: Variable region Heavy chain

<400> SEQUENCE: 13

Glu Val Gln Leu Val Glu Ser Gly Gly Leu Val Gln Pro Gly Arg
1               5                   10                  15

Ser Leu Arg Leu Ser Cys Ala Ala Ser Gly Phe Ser Phe Thr Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Leu Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Val Glu Asp Thr Ala Phe Tyr Tyr Cys
                85                  90                  95

Ala Lys Gly Met Ala Ala Ala Gly Asn Thr Asp Arg Phe Asp Tyr
            100                 105                 110

<210> SEQ ID NO 14
```

<211> LENGTH: 96
<212> TYPE: PRT
<213> ORGANISM: Artificial Sequence
<220> FEATURE:
<223> OTHER INFORMATION: Variable region Light chain

<400> SEQUENCE: 14

```
Ser Met Thr Gln Ser Pro Phe Ser Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Asp Pro Glu
65                  70                  75                  80

Asp Phe Ala Val Tyr Tyr Cys Gln Gln Tyr Gly Gly Ser Pro Ile Thr
                85                  90                  95
```

<210> SEQ ID NO 15
<211> LENGTH: 333
<212> TYPE: DNA
<213> ORGANISM: Artificial Sequence
<220> FEATURE:
<223> OTHER INFORMATION: Variable region Heavy chain

<400> SEQUENCE: 15

| | |
|---|---|
| gaggtgcagc tggtggagtc tgggggaggc ttggtacagc ctggcaggtc cctgagactc | 60 |
| tcctgtgcag cctctggatt cagctttact aattatgcca tgcactgggt ccggcaagct | 120 |
| ccagggaagg gcctggagtg gtctcaggt attagttgga atagtggtag catactctat | 180 |
| gcggactctg tgaagggccg attcaccatc tccagagaca acgccaagga ctccctgtat | 240 |
| ttgcaaatga acagtctgag agttgaggac acggccttct attactgtgc aaaaggaatg | 300 |
| gcagcagctg gaacactga ccgttttgac tac | 333 |

<210> SEQ ID NO 16
<211> LENGTH: 288
<212> TYPE: DNA
<213> ORGANISM: Artificial Sequence
<220> FEATURE:
<223> OTHER INFORMATION: Variable region Light chain

<400> SEQUENCE: 16

| | |
|---|---|
| tctatgaccc agtctccatt ctccctgtct ttgtctccag ggaaagagc caccctctcc | 60 |
| tgcagggcca gtcagagtgt tagcagcagc tacttagcct ggtaccagca gaaacctggc | 120 |
| caggctccca ggctcctcat ctatggtgca tccagcaggg ccactggcat cccagacagg | 180 |
| ttcagtggca gtgggtctgg gacagacttc actctcacca tcagcagact ggaccctgaa | 240 |
| gactttgcag tgtattactg tcagcaatat ggtggctcac cgatcacc | 288 |

<210> SEQ ID NO 17
<211> LENGTH: 122
<212> TYPE: PRT
<213> ORGANISM: Artificial Sequence
<220> FEATURE:
<223> OTHER INFORMATION: Variable region heavy chain

<400> SEQUENCE: 17

Glu Val Gln Leu Val Glu Ser Gly Gly Gly Leu Val Gln Pro Gly Arg

```
                 1               5                  10                 15
Ser Leu Arg Leu Ser Cys Ala Ala Ser Gly Phe Ser Phe Thr Asn Tyr
                20                 25                 30

Ala Met His Trp Val Arg Gln Ala Pro Gly Lys Gly Leu Glu Trp Val
                35                 40                 45

Ser Gly Ile Ser Trp Asn Ser Gly Ser Ile Leu Tyr Ala Asp Ser Val
                50                 55                 60

Lys Gly Arg Phe Thr Ile Ser Arg Asp Asn Ala Lys Asp Ser Leu Tyr
 65                 70                 75                 80

Leu Gln Met Asn Ser Leu Arg Val Glu Asp Thr Ala Phe Tyr Tyr Cys
                85                 90                 95

Ala Lys Gly Met Ala Ala Ala Gly Asn Thr Asp Arg Phe Asp Tyr Trp
               100                105                110

Gly Gln Gly Thr Leu Val Thr Val Ser Ser
               115                120

<210> SEQ ID NO 18
<211> LENGTH: 106
<212> TYPE: PRT
<213> ORGANISM: Artificial Sequence
<220> FEATURE:
<223> OTHER INFORMATION: variable region light chain

<400> SEQUENCE: 18

Ser Met Thr Gln Ser Pro Phe Ser Leu Ser Leu Ser Pro Gly Glu Arg
 1               5                  10                 15

Ala Thr Leu Ser Cys Arg Ala Ser Gln Ser Val Ser Ser Ser Tyr Leu
                20                 25                 30

Ala Trp Tyr Gln Gln Lys Pro Gly Gln Ala Pro Arg Leu Leu Ile Tyr
                35                 40                 45

Gly Ala Ser Ser Arg Ala Thr Gly Ile Pro Asp Arg Phe Ser Gly Ser
                50                 55                 60

Gly Ser Gly Thr Asp Phe Thr Leu Thr Ile Ser Arg Leu Asp Pro Glu
 65                 70                 75                 80

Asp Phe Ala Val Tyr Tyr Cys Gln Gln Tyr Gly Gly Ser Pro Ile Thr
                85                 90                 95

Phe Gly Gln Gly Thr Arg Leu Glu Ile Lys
               100                105

<210> SEQ ID NO 19
<211> LENGTH: 366
<212> TYPE: DNA
<213> ORGANISM: Artificial Sequence
<220> FEATURE:
<223> OTHER INFORMATION: variable region heavy chain

<400> SEQUENCE: 19
gaggtgcagc tggtggagtc tgggggaggc ttggtacagc ctggcaggtc cctgagactc     60
tcctgtgcag cctctggatt cagctttact aattatgcca tgcactgggt ccggcaagct    120
ccagggaagg gcctggagtg gtctcaggt attagttgga atagtggtag catactctat     180
gcggactctg tgaagggccg attcaccatc tccagagaca cgccaagga ctccctgtat     240 ttgcaaatga acagtctgag agttgaggac acggccttct attactgtgc aaaaggaatg    300
gcagcagctg gaaacactga ccgttttgac tactggggcc agggaaccct ggtcaccgtc    360
tcctca                                                              366
```

```
<210> SEQ ID NO 20
<211> LENGTH: 319
<212> TYPE: DNA
<213> ORGANISM: Artificial Sequence
<220> FEATURE:
<223> OTHER INFORMATION: variable region light chain

<400> SEQUENCE: 20
tctatgaccc agtctccatt ctccctgtct ttgtctccag gggaaagagc caccctctcc    60
tgcagggcca gtcagagtgt tagcagcagc tacttagcct ggtaccagca gaaacctggc   120
caggctccca ggctcctcat ctatggtgca tccagcaggg ccactggcat cccagacagg   180
ttcagtggca gtgggtctgg gacagacttc actctcacca tcagcagact ggaccctgaa   240
gactttgcag tgtattactg tcagcaatat ggtggctcac cgatcacctt cggccaaggg   300
acacgactgg agattaaac                                                319

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
acctgctgca aatgctgcgc                                                20

<210> SEQ ID NO 22
<211> LENGTH: 44
<212> TYPE: DNA
<213> ORGANISM: Artificial Sequence
<220> FEATURE:
<223> OTHER INFORMATION: primer

<400> SEQUENCE: 22
ctaatacgac tcactatagg gagaggttag cactttggct tggg                     44

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
aggcactcac catgggagct gaagtaaacg ttgatcaag                           39

<210> SEQ ID NO 24
<211> LENGTH: 39
<212> TYPE: DNA
<213> ORGANISM: Artificial Sequence
<220> FEATURE:
<223> OTHER INFORMATION: primer

<400> SEQUENCE: 24
gtgatgtcga attccgaatc cccaagcacc taaaccttg                           39

<210> SEQ ID NO 25
<211> LENGTH: 112
<212> TYPE: PRT
<213> ORGANISM: Artificial Sequence
<220> FEATURE:
<223> OTHER INFORMATION: 1D9 heavy chain

<400> SEQUENCE: 25
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Thr Asn Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Leu Tyr Ala Asp Ser Val
        50                  55                  60

Lys Gly Arg Phe Thr Ile Ser Arg Asp Asn Lys Asp Ser Leu Tyr
65                  70                  75                  80

Leu Gln Met Asn Ser Leu Arg Val Glu Asp Thr Ala Phe Tyr Tyr Cys
                85                  90                  95

Ala Lys Gly Met Ala Ala Ala Gly Asn Thr Asp Arg Phe Asp Tyr Trp
            100                 105                 110
```

<210> SEQ ID NO 26
<211> LENGTH: 97
<212> TYPE: PRT
<213> ORGANISM: Artificial Sequence
<220> FEATURE:
<223> OTHER INFORMATION: 1D9 light chain

<400> SEQUENCE: 26

```
Ser Met Thr Gln Ser Pro Phe Ser Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30

Ala Trp Tyr Gln Gln Lys Pro Gly Gln Ala Pro Arg Leu Leu Ile Tyr
            35                  40                  45

Gly Ala Ser Ser Arg Ala Thr Gly Ile Pro Asp Arg Phe Ser Gly Ser
        50                  55                  60

Gly Ser Gly Thr Asp Phe Thr Leu Thr Ile Ser Arg Leu Asp Pro Glu
65                  70                  75                  80

Asp Phe Ala Val Tyr Tyr Cys Gln Gln Tyr Gly Gly Ser Pro Ile Thr
                85                  90                  95

Phe
```

<210> SEQ ID NO 27
<211> LENGTH: 99
<212> TYPE: PRT
<213> ORGANISM: Artificial Sequence
<220> FEATURE:
<223> OTHER INFORMATION: IGHV3 heavy chain

<400> SEQUENCE: 27

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Lys Asp

<210> SEQ ID NO 28
<211> LENGTH: 96
<212> TYPE: PRT
<213> ORGANISM: Artificial Sequence
<220> FEATURE:
<223> OTHER INFORMATION: IGHV3 light chain

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

ANTIBODIES AGAINST *STAPHYLOCOCCUS AUREUS* AND USES THEROF

CROSS REFERENCE TO RELATED APPLICATIONS

This application is a U.S. National Stage of International Application No. PCT/NL2014/050857, filed Dec. 12, 2014, which claims the benefit of European application No. 13197211.9, filed Dec. 13, 2013, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Aug. 31, 2016, is named P102915US00 seqlist_ST25.txt and is 13.4 kilobytes in size.

The invention relates to the field of immunology and vaccine development. In particular, it relates to antibodies and fragments thereof against *Staphylococcus aureus* and to therapeutic and diagnostic uses thereof.

*S. aureus* can cause a wide variety of infections and represents a serious public health burden, particularly within health care settings. Antibiotic resistant forms of *S. aureus*, such as MRSA (Methicillin Resistant *S. aureus*), are prevalent within hospitals and lead to significantly increased mortality and length of stay for patients. Furthermore, the emergence of strains with reduced susceptibility to vancomycin, one of the antibiotics of last resort, is of increasing concern. Recent years have also witnessed a spread of resistant staphylococci outside health care settings and, alarmingly, community-acquired MRSA is now known to increase even in the absence of selective antibiotic pressure. Thus, the spectrum of resistant and untreatable staphylococcal infections has increased, and there is a high urgency to develop new anti-infective strategies.

Antibody therapy or "passive immune therapy" has been suggested to treat *S. aureus* infections (Keller M A et al. 2000. *Clin. Microbiol. Rev.* 13: 602; Projan S J M et al. 2006. *Curr. Opin. Pharmac.* 6:473). Antibody therapy has certain advantages above the current standard of care, i.e. antibiotics such as clindamycin or vancomycin. Passive immunization with human(ized) monoclonal antibodies seems a highly attractive alternative for antibiotics. Several anti-staphylococcal monoclonal antibodies have shown promise in animal studies and phase I clinical trials (Verkaik N J et al. 2011. Immunotherapy 2011; 3:1063-73). While these human(ized) monoclonal antibodies have proven to be safe, so far none of these therapeutics have shown sufficient efficacy to protect a sufficient number of patients against serious *S. aureus* infections in clinical studies. The bacterial targets of these antibodies were selected based on accessibility for antibody therapy and in some cases, a role in bacterial virulence. However, none of these monoclonals were designed to neutralize targets present on all *S. aureus* variants.

Therapeutic antibodies which bind only a fraction of the *S. aureus* strains that threaten patients and other (healthy) individuals, have failed to protect individuals who have been infected with strains which are not recognized by the antibodies.

A number of relevant properties of staphylococcal targets for passive immunization have been suggested. Potential targets should be (i) accessible for antibody therapy (located in extracellular bacterial compartments or surface attached), (ii) immunogenic (able to elicit an immune response), (iii) ubiquitously expressed within the variety of clinically relevant strains, and preferably (iv) critical for bacterial virulence.

Anti-staphylococcal antibodies also find their use in diagnostic applications, in particular diagnosis of (suspected) infections following implantation. Whereas a number of technical and operative improvements for the use of prosthetics has reduced the risk of infection, the increasing number of joint replacements and other implantations being performed means the absolute number of such infections will remain significant and pose substantial costs to healthcare systems worldwide. Diagnosis is often challenging as symptoms are variable and most currently available diagnostic tests are non-specific. Delayed diagnosis may lead to reduced function, increased morbidity and the need for more complex surgery, often involving multiple procedures. Early diagnosis, selection of an appropriate surgical strategy, accurate identification of the responsible microorganisms and construction of an appropriate antibiotic regimen are essential elements of any management strategy.

Recognizing the need for specific antibodies which are 'broadly neutralizing', in order to protect a large number of patients, the present inventors set out to generate broadly neutralizing anti-staphylococcal antibodies i.e. which bind to the largest possible variety of *S. aureus* types but show sufficient specificity. To that end, they isolated human monoclonal antibodies from subjects who had previously been exposed to skin infections by multiple, and variable *S. aureus* types. After the generation and identification of monoclonal antibodies from these selected subjects, it was tested whether the antibodies indeed specifically recognized a large variety of *S. aureus* strains.

It was surprisingly found that monoclonal antibodies cloned from polyclonal B-cells obtained from the peripheral blood of an *S. aureus*-carrying human donor could specifically bind the Immunodominant staphylococcal antigen A (IsaA) at nM concentrations. The human anti-IsaA IgG1 mAb 1D9 was shown to bind to all 26 *S. aureus* strains tested, including methicillin-susceptible and methicillin-resistant *S. aureus* strains (MSSA and MRSA, respectively). Importantly, in mice with *S. aureus* isolate P bacteremia, prophylactic treatment with a single dose of 5 mg/kg 1D9 improved survival of mice. The amino acid sequence of the antigen-recognizing parts (CDRs) of the human antibody was determined (see FIG. 1).

Accordingly, the invention provides an isolated human or humanized antibody or a functional fragment thereof, which binds to an epitope of the Immunodominant staphylococcal antigen A (IsaA), wherein said antibody comprises the *Staphylococcus* IsaA epitope-binding CDR sequences represented by the amino acid sequences SEQ ID NO: 1; SEQ ID NO: 2; SEQ ID NO: 3; SEQ ID NO: 4; SEQ ID NO: 5 and SEQ ID NO: 6 (see Table 1), and functional equivalents thereof having an amino acid sequence that is at least 85% identical to an amino acid sequence of SEQ ID NO: 1-6.

TABLE 1

| SEQ ID NO: | Identity | Sequence |
|---|---|---|
| 1 | Heavy chain CDR1 | GFSFTNYA |
| 2 | Heavy chain CDR2 | ISWNSGSI |
| 3 | Heavy chain CDR3 | AKGMAAAGNTDRFDY |
| 4 | Light chain CDR1 | QSVSSSY |
| 5 | Light chain CDR2 | GAS |
| 6 | Light chain CDR3 | QQYGGSPIT |
| 7 | Heavy chain CDR1 | ttc agc ttt act aat tat gcc |
| 8 | Heavy chain CDR2 | att agt tgg aat agt ggt agc ata |
| 9 | Heavy chain CDR3 | gca aaa gga atg gca gca gct ggg aac act gac cgt ttt gac tac |
| 10 | Light chain CDR1 | cag agt gtt agc agc agc tac |
| 11 | Light chain CDR2 | ggt gca tcc |
| 12 | Light chain CDR3 | cag caa tat ggt ggc tca ccg atc acc |
| 13 | Variable region Heavy chain | EVQLVESGGGLVQPGRSLRLSCAASGFSFTNY AMHWVRQAPGKGLEWVSGISWNSGSILYAD SVKGRFTISRDNAKDSLYLQMNSLRVEDTAF YYCAKGMAAAGNTDRFDY |
| 14 | Variable region Light chain | SMTQSPFSLSLSPGERATLSCRASQSVSSSYLA WYQQKPGQAPRLLIYGASSRATGIPDRFSGSG SGTDFTLTISRLDPEDFAVYYCQQYGGSPIT |
| 15 | Variable region Heavy chain | gaggtgcagctggtggagtctgggggaggcttggtacagcctggc aggtccctgagactctcctgtgcagcctctggattcagctttactaat tatgccatgcactgggtccggcaagctccagggaagggcctggagt gggtctcaggtattagttggaatagtggtagcatactctatgcgga ctctgtgaagggccgattcaccatctccagagacaacgccaaggac tccctgtatttgcaaatgaacagtctgagagttgaggacacggcctt ctattactgtgcaaaaggaatggcagcagctgggaacactgaccg ttttgactac |
| 16 | Variable region Light chain | tctatgacccagtctccattctccctgtctttgtctccaggggaaaga gccaccctctcctgcagggccagtcagagtgttagcagcagctactt agcctggtaccagcagaaacctggccaggctcccaggctcctcatct atggtgcatccagcagggccactggcatcccagacaggttcagtgg cagtgggtctgggacagacttcactctcaccatcagcagactggac cctgaagactttgcagtgtattactgtcagcaatatggtggctcacc gatcacc |
| 17 | Variable region Heavy chain* | EVQLVESGGGLVQPGRSLRLSCAASGFSFTNY AMHWVRQAPGKGLEWVSGISWNSGSILYAD SVKGRFTISRDNAKDSLYLQMNSLRVEDTAF YYCAKGMAAAGNTDRFDYWGQGTLVTVSS |
| 18 | Variable region Light chain * | SMTQSPFSLSLSPGERATLSCRASQSVSSSYLA WYQQKPGQAPRLLIYGASSRATGIPDRFSGSG SGTDFTLTISRLDPEDFAVYYCQQYGGSPITF GQGTRLEIK |
| 19 | Variable region Heavy chain* | gaggtgcagctggtggagtctgggggaggcttggtacagcctggc aggtccctgagactctcctgtgcagcctctggattcagctttactaat tatgccatgcactgggtccggcaagctccagggaagggcctggagt gggtctcaggtattagttggaatagtggtagcatactctatgcgga ctctgtgaagggccgattcaccatctccagagacaacgccaaggac tccctgtatttgcaaatgaacagtctgagagttgaggacacggcctt ctattactgtgcaaaaggaatggcagcagctgggaacactgaccg ttttgactactggggccagggaaccctggtcaccgtctcctca |
| 20 | Variable region Light chain* | tctatgacccagtctccattctccctgtctttgtctccaggggaaaga gccaccctctcctgcagggccagtcagagtgttagcagcagctactt agcctggtaccagcagaaacctggccaggctcccaggctcctcatct atggtgcatccagcagggccactggcatcccagacaggttcagtgg |

TABLE 1-continued

| SEQ ID NO: | Identity | Sequence |
|---|---|---|
| | | cagtgggtctgggacagacttcactctcaccatcagcagactggac cctgaagactttgcagtgtattactgtcagcaatatggtggctcacc gatcaccttcggccaagggacacgactggagattaaac |

*Including the FR4 sequence

Surface antigen IsaA, or "Immunodominant staphylococcal antigen A" is well known in the art (Lorenz et al. 2000 FEMS Immunol. Med. Microb. 29: 145; Sakata N et al. 2005. Curr. Microbiol. 50: 47). IsaA has been recognized as an 'invariant' target, being ubiquitously present on all investigated clinical S. aureus strains (Ziebandt A K et al. 2010. Proteomics. 10:1634). Recently, IsaA has been identified as an effective target in antibody therapy by showing that mouse monoclonal antibodies against IsaA protect animals against lethal S. aureus infections (Lorenz et al. 2011 Antimicrob. Agents Chemother. 55: 165). See also WO2010/133600 disclosing monoclonal antibodies directed against epitopes of IsaA as primary antibodies that were produced by the hybridoma cell line DSM ACC2987 and that are designated as MAB-UK-66. In WO 2013/041707, the inventors modified the binding region of one of the antibodies known from WO 2010/133600 and thereby developed a binding site that is more effective in support of killing of S. aureus by phagocytosis by phagocytizing blood. However, the murine monoclonal antibodies disclosed in the art are distinct from a human IsaA-antibody of the present invention.

The term "antibody" is used herein in the broadest sense and specifically covers monoclonal antibodies (including full length monoclonal antibodies) of any isotype such as IgG, IgM, IgA, IgD, and IgE, polyclonal antibodies, multi-specific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

An antibody or fragment thereof as provided herein recognizes native IsaA and is able to bind to whole cell S. aureus, in particular to S. aureus isolate P, and to MRSA strain S. aureus USA300.

A typical antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions". As used herein, "VH" or "VH" refers to the variable region of an immunoglobulin heavy chain of an antibody, including the heavy chain of an Fv, scFv, dsFv, Fab, Fab', or F(ab')2 fragment. Reference to "VL" or "VL" refers to the variable region of the immunoglobulin light chain of an antibody, including the light chain of an Fv, scFv, dsFv, Fab, Fab', or F(ab')2 fragment.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

A "functional part of an antibody" or "functional fragment" refers to a portion of a full-length antibody, which portion is generally the target binding or variable region. Examples of antibody fragments include Fab, Fab', F(ab')2 and Fv fragments. The phrase "functional fragment or analog" of an antibody is a compound having qualitative biological activity in common with a full-length antibody, albeit not necessarily to the same extent. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer Collectively, the six CDRs confer target binding specificity to the antibody. However, even a single variable domain (or half of an Fv comprising only three CDRs specific for an target) may have the ability to recognize and bind target. "Single-chain Fv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')2 pepsin digestion product. Additional chemical couplings of antibody fragments are known to those of ordinary skill in the art. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single targeting site, called the antibody determinant or epitope. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well-known techniques.

The antibody or fragment thereof comprises the six *Staphylococcus* IsaA epitope-binding CDR sequences represented by SEQ ID NO: 1; SEQ ID NO: 2; SEQ ID NO: 3; SEQ ID NO: 4; SEQ ID NO: 5 and SEQ ID NO: 6, wherein one or more of the CDRs can be a functional equivalent of the respective sequences having an amino acid sequence that is at least 85% identical to an amino acid sequence of SEQ ID NO: 1-6 and which binds to an epitope of the Staphylococcal IsaA epitope. Preferably, a functional equivalent of a *Staphylococcus* IsaA epitope-binding CDR sequence has an amino acid sequence that is at least 90%, preferably at least 91%, 92%, 93% or 94% more preferably at least 95%, 96%, 97%, 98% or 99% identical to an amino acid sequence of SEQ ID NO: 1-6. The CDR amino acid sequences can be encoded by one or more of the nucleotide sequences of SEQ ID NO: 7-12. However, variations may be present within these nucleotide sequences, e.g. due to the redundancy of the genetic code, exhibited as the multiplicity of three-codon combinations specifying a given amino acid.

In one aspect, there is provided an antibody or fragment thereof, having a heavy chain sequence comprising a sequence which is at least 85% identical to the sequence of SEQ ID NO: 13 or SEQ ID NO: 17 and/or having a light chain sequence which is at least 85% identical to the sequence of SEQ ID NO: 14 or SEQ ID NO: 18. For example, the heavy chain sequence is at least 87%, preferably at least 90%, 92%, 93%, 94%, 95%, 96%, 97%, 98% or 99% identical to the sequence of SEQ ID NO: 13 and/or the light chain sequence is at least 87%, preferably at least 90%, 92%, 93%, 94%, 95%, 96%, 97%, 98% or 99% identical to the sequence of SEQ ID NO: 14. In one aspect, the heavy chain sequence is at least 87%, preferably at least 90%, 92%, 93%, 94%, 95%, 96%, 97%, 98% or 99% identical to the sequence of SEQ ID NO: 17 and/or the light chain sequence is at least 87%, preferably at least 90%, 92%, 93%, 94%, 95%, 96%, 97%, 98% or 99% identical to the sequence of SEQ ID NO: 18.

The human light chain IgV[kappa] and J[kappa] germline genes and heavy chain IgVh and Jh germline genes from which 1D9 was likely derived have been identified, as disclosed in the experimental Examples section. Such germline gene sequences are useful to identify somatic mutations in the antibodies, including in the CDRs. Accordingly, in one embodiment, the antibody or fragment thereof comprises at least one mutation in the germ-line heavy-chain and/or kappa-chain sequence according to FIG. 1. In particular, the one or more germline mutation in the heavy chain is selected from the group consisting of: position 29 S→T; position 35 T→D; position 36 N→D; position 66 L→G; position 85 D→N; position 96 V→A; position 101 F→L; and position 107 G→D, wherein the position number is defined as in FIG. 1; in particular, the one or more germline mutations in the light chain are selected from the group consisting of position 3 S→V; position 4 M→L; position 9 F→G; position 10 S→T; position 95 D→E; and position 109 G→S, wherein the position number is defined as in FIG. 1.

In a specific aspect, the antibody has a heavy chain comprising a sequence according to the sequence of SEQ ID NO: 13, preferably SEQ ID NO: 17, and a light chain sequence according to the sequence of SEQ ID NO: 14, preferably SEQ ID NO: 18. This antibody is herein referred to as mAb 1D9.

In one embodiment, the IsaA-specific antibody or fragment thereof is a human or humanized antibody. As used herein, the term "humanized antibody" refers to a chimeric antibody which contains a minimal sequence derived from non-human immunoglobulin. A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. Sci. U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

Antibodies with homologous sequences are those antibodies with amino acid sequences that have sequence homology with amino acid sequence of an anti-IsaA antibody of the present invention. Preferably homology is with the amino acid sequence of the variable regions of the anti-IsaA. "Sequence homology" as applied to an amino acid sequence herein is defined as a sequence with at least about 90%, 91%, 92%, 93%, or 94% sequence homology, and more preferably at least about 95%, 96%, 97%, 98%, or 99% sequence homology to another amino acid sequence, as determined, for example, by the FASTA search method in accordance with Pearson and Lipman, 1988, Proc. Natl. Acad. Sci. U.S.A., 85: 2444-2448.

A chimeric antibody is one in which different portions of an antibody are derived from different animal species. For example, an antibody having a variable region derived from a murine monoclonal antibody paired with a human immunoglobulin constant region. Methods for producing chimeric antibodies are known in the art. See, e.g., Morrison, 1985, Science, 229: 1202; Oi et al., 1986, Bio Techniques, 4: 214; Gillies et al., 1989, J. Immunol. Methods, 125: 191-202; U.S. Pat. Nos. 5,807,715; 4,816,567; and 4,816,397.

Artificial antibodies include scFv fragments, diabodies, triabodies, tetrabodies and mru (see reviews by Winter, G. and Milstein, C., 1991, Nature, 349: 293-299; Hudson, P. J., 1999, Current Opinion in Immunology, 11: 548-557), each of which has antigen-binding ability. In the single chain Fv fragment (scFv), the VH and VL domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mru's can be linked together with short linker peptides, therefore forming an artificial binding protein with higher avidity than a single mru.

The functional equivalents of the present application also include modified IsaA antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, conjugation with fluorophores (fluorescein isothiocyanate [FITC], indocyanin green [ICG] and IRDye800CW) or conjugation with radioisotopes ($^{99m}$Technetium, $^{18}$Fluorine, $^{201}$Thallium, $^{123}$Iodine), etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art. The antibody fragments and functional equivalents of the present invention encompass those molecules with a detectable degree of binding to IsaA, when compared to the 1D9 antibody. A detectable degree of binding includes all values in the range of at least 10-100%, preferably at least 50%, 60% or 70%, more preferably at least 75%, 80%, 85%, 90%, 95% or 99% the binding ability of the 1D9 antibody to IsaA.

Preferably, the antibody fragments and functional equivalents of the present invention encompass those molecules with a detectable degree of prophylactic effect in mice against S. aureus bacteremia when compared to the 1D9 antibody. A detectable degree of prophylaxis includes all values in the range of at least 10-100%, preferably at least 50%, 60% or 70%, more preferably at least 75%, 80%, 85%, 90%, 95% or 99% the effect obtained, e.g. with a single dose of 5 mg/kg, of the 1D9 antibody.

The CDRs are generally considered of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made. Thus, also included in the scope of the present invention are improved versions of both the murine and humanized antibodies, which also specifically recognize and bind IsaA, preferably with increased affinity. Several studies have surveyed the effects of introducing one or more amino acid changes at various positions in the sequence of an antibody, based on the knowledge of the primary antibody sequence, on its properties such as binding and level of expression (Yang, W. P. et al., 1995, J. Mol. Biol., 254: 392-403; Rader, C. et al., 1998, Proc. Natl. Acad. Sci. U.S.A., 95: 8910-8915; Vaughan, T. J. et al., 1998, Nature Biotechnology, 16: 535-539). In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of E. coli. By a similar directed strategy of changing one or more amino acid residues of the antibody, the antibody sequences described in this invention can be used to develop anti-IsaA antibodies with improved functions, including improved binding to S. aureus.

Preferred amino acid substitutions are those which: (1) reduce susceptibility to proteolysis, (2) reduce susceptibility to oxidation, (3) alter binding affinity for forming protein complexes, and (4) confer or modify other physico-chemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts. A conservative amino acid substitution should not substantially change the structural characteristics of the parent sequence e.g., a replacement amino acid should not tend to break a helix that occurs in the parent sequence, or disrupt other types of secondary structure that characterizes the parent sequence). Improved antibodies also include those antibodies having improved characteristics that are prepared by the standard techniques of animal immunization, hybridoma formation and selection for antibodies with specific characteristics.

A further aspect relates to nucleic acids encoding anti-IsA antibodies of the invention. In one embodiment, the nucleic acid molecule encodes a heavy and/or a light chain of an anti-IsaA immunoglobulin. In a preferred embodiment, a single nucleic acid encodes a heavy chain of an anti-IsaA immunoglobulin and another nucleic acid molecule encodes the light chain of an anti-IsaA immunoglobulin.

In one embodiment, there is provided an isolated, synthetic or recombinant nucleic acid sequence encoding a polypeptide sequence according to SEQ ID NO: 13, 14, 17 or 18 or a sequence which has at least 85%, preferably at least 90%, sequence identity therewith. In a preferred embodiment, the polynucleotide comprises a sequence which is at least 95% identical to SEQ ID NO: 15 or SEQ ID NO: 19 and/or a sequence which is at least 95% identical to SEQ ID NO: 16 or SEQ ID NO: 20. In a specific embodiment, the nucleic acid sequence comprises a sequence which is at least 98% identical to SEQ ID NO: 15 and/or a sequence which is at least 98% identical to SEQ ID NO: 16. In another specific embodiment, the nucleic acid sequence comprises a sequence which is at least 98% identical to SEQ ID NO: 19 and/or a sequence which is at least 98% identical to SEQ ID NO: 20.

The invention provides vectors comprising the polynucleotides of the invention. In one embodiment, the vector contains a polynucleotide encoding a heavy chain of an anti-IsaA immunoglobulin. In another embodiment, said polynucleotide encodes the light chain of an anti-IsaA immunoglobulin. The invention also provides vectors comprising polynucleotide molecules encoding fusion proteins, modified antibodies, antibody fragments, and probes thereof. In order to express the heavy and/or light chain of the anti-IsaA antibodies of the invention, the polynucleotides encoding said heavy and/or light chains are inserted into expression vectors such that the genes are operatively linked to transcriptional and translational sequences. Expression vectors include plasmids, YACs, cosmids, retrovirus, EBV-derived episomes, and all the other vectors that the skilled man will know to be convenient for ensuring the expression of said heavy and/or light chains. The skilled man will realize that the polynucleotides encoding the heavy and the light chains can be cloned into different vectors or in the same vector. In a preferred embodiment, said polynucleotides are cloned in the same vector.

Polynucleotides of the invention and vectors comprising these molecules can be used for the transformation of a suitable mammalian host cell, or any other type of host cell known to the skilled person. Transformation can be by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

In one embodiment, an isolated antibody or a functional fragment thereof according the invention is used as a medicament and/or prophylactic agent. Also provided is a method for prophylactic or therapeutic treatment of a human being or animal which has an infection with an IsaA-expressing microorganism, comprising administering an antibody or antibody fragment of the invention. Preferably, the subject has, or is suspected to have, an infection with *Staphylococcus aureus*, especially methicillin resistant or methicillin sensitive *Staphylococcus aureus*, or is at risk of getting such an infection. In one aspect, the antibody is used in a method of decreasing the risk of developing an infection caused by an IsaA-expressing microorganism in a subject. In another embodiment, the antibody is used in a method of alleviating a symptom of an infection caused by an IsaA-expressing microorganism in a subject. In a preferred embodiment, antibodies or antibody fragments of the invention are used for the prophylactic or therapeutic treatment of a human being or animal which has, or is suspected to have, an infection with an IsaA-expressing microorganism, preferably *Staphylococcus aureus*, especially methicillin resistant or methicillin sensitive *Staphylococcus aureus*, or is at risk of getting such an infection. In one aspect, the antibody is used in a method of decreasing the risk of developing an infection caused by an IsaA-expressing microorganism in a subject. In another embodiment, the antibody is used in a method of alleviating a symptom of an infection caused by an IsaA-expressing microorganism in a subject. The antibody or a functional fragment thereof can be administered before, after or during infection with said IsaA-expressing microorganism. The antibodies or fragments may be administered systemically, in particular intravenously, nasally, sublingually, or topically.

Also provided herein is a pharmaceutical composition comprising an isolated IsaA-antibody or a functional fragment thereof according to the invention and a pharmaceutically acceptable carrier, diluent and/or excipient. The composition may further comprise at least one further active ingredient. For example, the anti-IsaA antibody of the invention is combined with a (monoclonal) antibody directed against at least one further epitope of *Staphylococcus aureus*. Preferably, the antibody is combined with one or more human mAbs targeting other conserved *S. aureus* antigen(s). This further epitope may be located on the antigen on which the epitope is located, i.e. IsaA, or on a further antigen. The use of such a mixture as a medicament may be more efficient than the use of a medicament which solely contains the antibodies or fragments according to the invention. This may be owing to the high variability of *S. aureus* that causes different extents of expression of the antigens on different strains such that more bacteria are recognized by the mixture of antibodies or fragments than by the antibodies or fragments alone. Furthermore, the antibodie(s) may be combined with any other useful drug substance designed to cure, alleviate, remove or lessen the symptoms of, or prevent or reduce the possibility of contracting such an infection. In a specific aspect, the anti-IsaA antibody of the invention is combined with a glycopeptide antibiotic such as vancomycin, teicoplanin or daptomycin.

The antibodies or antibody fragments of the invention can also be used as diagnostic reagent to detect an IsaA-expressing microorganism, e.g. in a biological sample. Detection can be in vitro or in vivo. For example, provided herein is a method for *S. aureus*, preferably MRSA, detection comprising the steps of: contacting a test sample with an IsaA-specific antibody of the invention; and detecting the formation of an antigen-antibody complex.

For the purpose of diagnostic applications, the antibody is advantageously provided with a detection label capable of producing detectable signals. Such detection label can be one or more selected from the group consisting of enzymes, fluorescent substances, luminescent and radioactive materials. In more detail, the examples of detection label include various enzymes, prosthetic groups, fluorescent materials, luminescent materials, bioluminescent materials radioactive materials.

The detection label can be coupled or bound to the monoclonal antibodies according to the present inventions, directly or indirectly via a coupler (i.e., linkers known in this field). Examples of suitable enzymes include: horse radish peroxidase, acetylcholinesterase, peroxidase, alkaline phosphatase, [beta]-D-galactosidase, glucose oxidase, malate dehydrogenase, Glucose-6-phosphate dehydrogenase, and invertase. Examples of suitable prosthetic groups include: streptavidin/biotin and avidin/biotin. Examples of suitable fluorescent materials include: umbelliferon. fluorescein, fluorescein isothiocyanate, rhodamine, dichlorotriazinyl amine fluorescein, dansyl chloride, phycoerythrin and phycobiliprotein. Examples of suitable luminescent materials include: luminal, isoluminol, and lucigenin. Examples of suitable bioluminescent materials include: luciferases, luciferin and aequorin. Examples of suitable radioactive materials include: <125>I, <131>I, <111>In, <99>Tc, <14>C, and <3>H.

In one embodiment, a labeled IsaA-specific antibody is used for targeted bacterial imaging, e.g. to detect, diagnose and/or treat a bacterial infection. Bacterial infections represent an increasing problem in modern health care, in particular due to ageing populations and accumulating bacterial resistance to antibiotics. Diagnosis is rarely straightforward and consequently treatment is often indefinite. Therefore, novel tools that can be clinically implemented are urgently needed to accurately diagnose infections. Especially, the direct imaging of infections is an attractive option. The challenge of specifically imaging bacterial infections in vivo can be met by targeting bacteria with an imaging agent, as exemplified by recent developments in molecular imaging and optical imaging. This was recently highlighted by the use of so-called smart activatable probes and a fluorescently labelled derivative of the antibiotic vancomycin. Importantly, the spectrum of potential applications for targeted bacterial imaging ranges from diagnostic to therapeutic applications, including targeted photodynamic therapy.

In a specific embodiment, the invention provides the IsaA-specific antibody for use in a diagnostic method comprising the administration of the antibody intravenously to a subject, preferably a human subject, suspected or known to suffer from an infection by S. aureus or any other IsaA-expressing organism. For example, the subject has undergone an implantation surgery, and is to be diagnosed for an infection of the implant.

In a specific embodiment, the IsaA-antibody conjugated to a fluorophore or a radioactive label is used for in vivo imaging, preferably non-invasive imaging. Suitable fluorophores include fluorescein isothiocyanate [FITC], indocyanin green [ICG] or IRDye800CW. Suitable radioisotopes include $^{99m}$Technetium, $^{18}$Fluorine, $^{291}$Thallium and $^{123}$Iodine. For example, the fluorescently labelled IsaA-antibody is advantageously used to specifically target and detect an infection by S. aureus or any other IsaA-expressing organism. This allows for real time in vivo imaging and enhanced non-invasive diagnosis, e.g. (sterile) infections on knee- or hip-implants. In fact, an IsaA-antibody of the invention can be used as a specific bacterial probe in combination with a multispectral NIR clinical imaging camera, as has recently been described for fluorescently labeled vancomycin (Van Oosten et al. (2013) Nature Comm. 4:2584). In a specific aspect, the invention provides mAb 1D9 conjugated to an infrared dye, preferably IRDye800CW.

In a still further embodiment, the IsaA-antibody is used as targeting moiety in a therapy against an infection by S. aureus or any other IsaA-expressing organism. For example, it is conjugated to a therapeutic compound or precursor thereof. In a specific aspect, it is used as targeting moiety in photodynamic therapy (PDT). PDT was discovered over 100 years ago by observing the killing of microorganisms when harmless dyes and visible light were combined in vitro. Since then it has primarily been developed as a treatment for cancer, ophthalmologic disorders, and in dermatology. However in recent years interest in the antimicrobial effects of PDT has been revived, motivated by the rapidly increasing emergence of antibiotic resistance amongst pathogenic bacteria, and it has been proposed as a therapy for a large variety of localized infections. PDT provides significant advantages over existing antimicrobial therapies. It appears equally effective to kill multi-drug resistance microbes as naïve strains, and acts remarkably faster against microorganisms than antimicrobials. Another exemplary advantage of photodynamic disinfection as a MRSA treatment modality is that, due to this non-specific bactericidal mechanism, it is typically not subject to issues of resistance that can plague the use of antibiotics. As yet another exemplary advantage, it can be employed as a localized topical treatment that can be administered in areas such as the nasal cavities (e.g., nasal mucosa) where MRSA is mostly likely found in the human body. One potential problem associated with PDT of infectious diseases is its lack of specificity. Hence, if the photosensitiser binds to, or is taken up by, a host cell, as well as the target organism, then subsequent irradiation may also lead to the death of the host cell. A way to overcome this is by the use of targeting compounds: that is, any compound that is capable of specifically binding to the surface of the pathogen.

An IsaA-antibody of the invention is therefore advantageously conjugated to an effective antimicrobial photosensitizer (PS). Preferably, the photosensitiser is chosen from Porphyrins, phthalocyanines, chlorins, bacteriochlorins, phenothiaziniums, phenazines, acridines, texaphyrins, cyanines, anthracyclins, pheophorbides, sapphyrins, fullerene, halogenated xanthenes, perylenequinonoid pigments, gilvocarcins, terthiophenes, benzophenanthridines, psoralens and riboflavin. In a specific aspect, the photosensitiser is tin (IV) chlorin e6 (SnCe6). Also provided herein is the use of a PS-conjugated antibody for binding to bacteria together with the use of light having a wavelength absorbable by the photosensitizer of said conjugate, in the treatment of bacterial infection.

Still further, the invention provides a method of killing bacteria, comprising (a) contacting the area to be treated with a PS-conjugated IsaA-antibody as defined herein above, such that any bacteria present bind to the photosensitiser-bacteria conjugate; and (b) irradiating the area with light at a wavelength absorbed by the photosensitiser, wherein said method is not a method of medical treatment. Preferably, the bacteria are *staphylococcus*, more preferably the bacteria are MRSA, EMRSA, VRSA, hetero-VRSA or CA-MRSA. Typically, the light is laser light or white light, or the source of light is a light emitting dioide.

The invention also provides a diagnostic kit comprising an IsaA-specific antibody. In one embodiment, the kit is an MRSA detection kit. The kit may comprise one or more further detection means and reagents, like further antibodies such as a Protein A-specific antibody and/or a PBP2a-specific antibody. Kit systems that can be used for the present invention include ELISA plates, a deep-stick device, an immunochromatographic assay, radial partition immunoassay device, a flow-through device, etc. Preferably, a diagnostic kit provided in immunochromatographic strip or device form can be used. In immunochromatographic diagnosis, antigens contained in a testing serum react with tracer antibody bound to colloidal gold particle. Then, while migrating through micropores on the nitrocellulose membrane by capillary action, the antigens are bound to capture antibody to produce color development on the strip, such that positive and negative signals are observable by naked eye. Such kit can preferably employ ELISA or lateral flow immunographic assay.

A kit that can be used for the present invention can be, one comprising: solid phase support; the monoclonal antibodies according to the present invention; and ELISA reaction fluids containing enzyme-labeled antibody solution for reacting with antigen and a dye reagent for signaling enzyme reaction. In more detail, said enzyme-labeled antibody solution can be of goat anti-mouse Ig-HRP (50-150 [mu]l per well at appropriate concentrations). The dye reagent can be selected from the group consisting of tetramethylbenzidines (TMB). Stopping solution can be selected from the group consisting of 1N HCl and 1N $H_2SO_4$.

LEGEND TO THE FIGURES

FIG. 1. 1D9 amino acid sequence. Human monoclonal IgG1 antibodies were generated using the mCHR protocol (molecular Cloning of the Human Response). Monoclonal antibodies were purified using protein A agarose beads and tested for specific binding to IsaA-His6 by ELISA. The IgG1 genes for the IsaA-specific monoclonal antibody 1D9 were sequenced and the translated sequence was compared to that of IgG1 sequences deposited in the NCBI database as shown.

FIG. 2. Donor selection and generation of human monoclonal antibody 1D9 specific for IsaA and *S. aureus*. (A) Serum IgG levels against IsaA-His$_6$ (upper panel) or PA (lower panel) in 6 nasal *S. aureus* carriers. (B) Concentration-dependent binding of mAb 1D9 and isotype control antibody (IQNPA) to IsaA-His$_6$ (upper panel) or BSA (lower panel). (C) Binding of mAb 1D9 to native and IsaA-His$_6$. Western blot analysis of native IsaA in cell (cell) and supernatant (sup) fractions of *S. aureus* SH1000Δspa and purified IsaA-His$_6$ using 1D9 (left panel) or rabbit polyclonal anti-IsaA (right panel) (D) Concentration-dependent binding of mAb 1D9 and isotype control antibody IQNPA to *S. aureus* Newman ΔspaΔsbi in mid-exponential growth.

FIG. 3. Binding of mAb 1D9 to *S. aureus* in whole cell ELISA assay. Plates were coated with cells of various *S. aureus* strains harvested at mid-exponential growth. Biotinylated mAb 1D9 or isotype control antibody IQNPA were added. Absorption values (at $OD_{450}$) are plotted relative to binding of 1000 ng/mL 1D9 to *S. aureus* Newman ΔspaΔsbi. Experiments were performed in duplicate. Mean±SD is shown. (A) Concentration-dependent binding of mAb 1D9 to *S. aureus* Newman ΔspaΔsbi, Newman wild-type (WT), isolate P, or MRSA USA300. (B) Concentration-dependent binding of isotype control antibody IQNPA to *S. aureus* Newman ΔspaΔsbi, Newman wild-type (WT), isolate P, or USA300. (C) Binding of 100 ng/mL mAb 1D9 to *S. aureus* Newman ΔspaΔsbi, various clinical *S. aureus* isolates including *S. aureus* isolate P, or the sequenced *S. aureus* strains Mu50, MW2, N315, COL, 8325-4, MRSA252, MSSA476, USA300 and Newman. (D) Binding of 100 ng/mL isotype control antibody IQNPA to *S. aureus* Newman ΔspaΔsbi, various clinical *S. aureus* isolates including *S. aureus* isolate P, or various sequenced *S. aureus* strains as specified for panel C.

FIG. 4. Activation of human and mouse neutrophils by mAb 1D9. Plates were coated with 5 μg/mL HSA (A, C) or IsaA (B, D), blocked with 10% fetal calf serum and incubated with 1 or 3 μg/mL rabbit anti-HSA or mAb 1D9, respectively. Control antibodies were normal rabbit IgG or human control mAb IQNPA. Neutrophils (human neutrophils (A, B) $1.25\times10^6$ cells/mL, mouse neutrophils (C, D) $5\times10^6$ cells/mL) were added to initiate the reaction. Oxidative burst was measured for 30 minutes at 37° C. RLU, relative light units.

Figure 5:
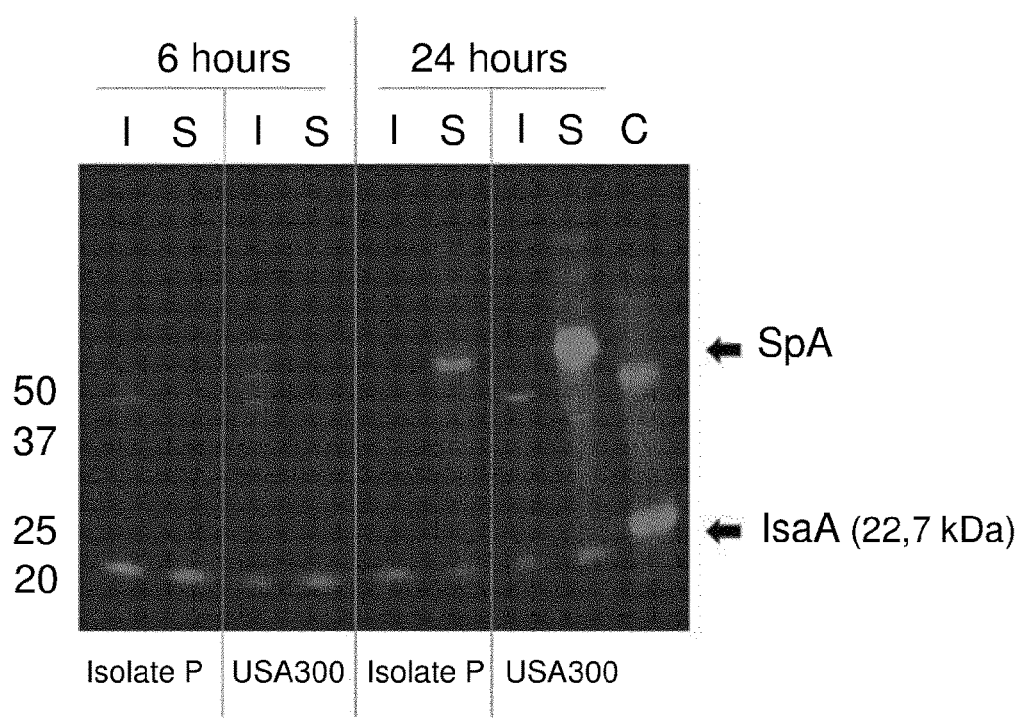

FIG. 5. Immunodetection of the expression of IsaA by *S. aureus* isolate P and *S. aureus* USA300. Both strains were grown in IMCM (I) or mouse serum (S) and after 6 or 24 hours culture samples were taken. Equal amounts of cellular proteins collected at the different time points from each culture were loaded based on the determined number of cfu as described in the Materials and Methods. As a positive control for immunodetection, isolated IsaA-His$_6$ was used (C). Bands specific for IsaA or the staphylococcal protein A (Spa) are marked with arrows.

Figure 6:
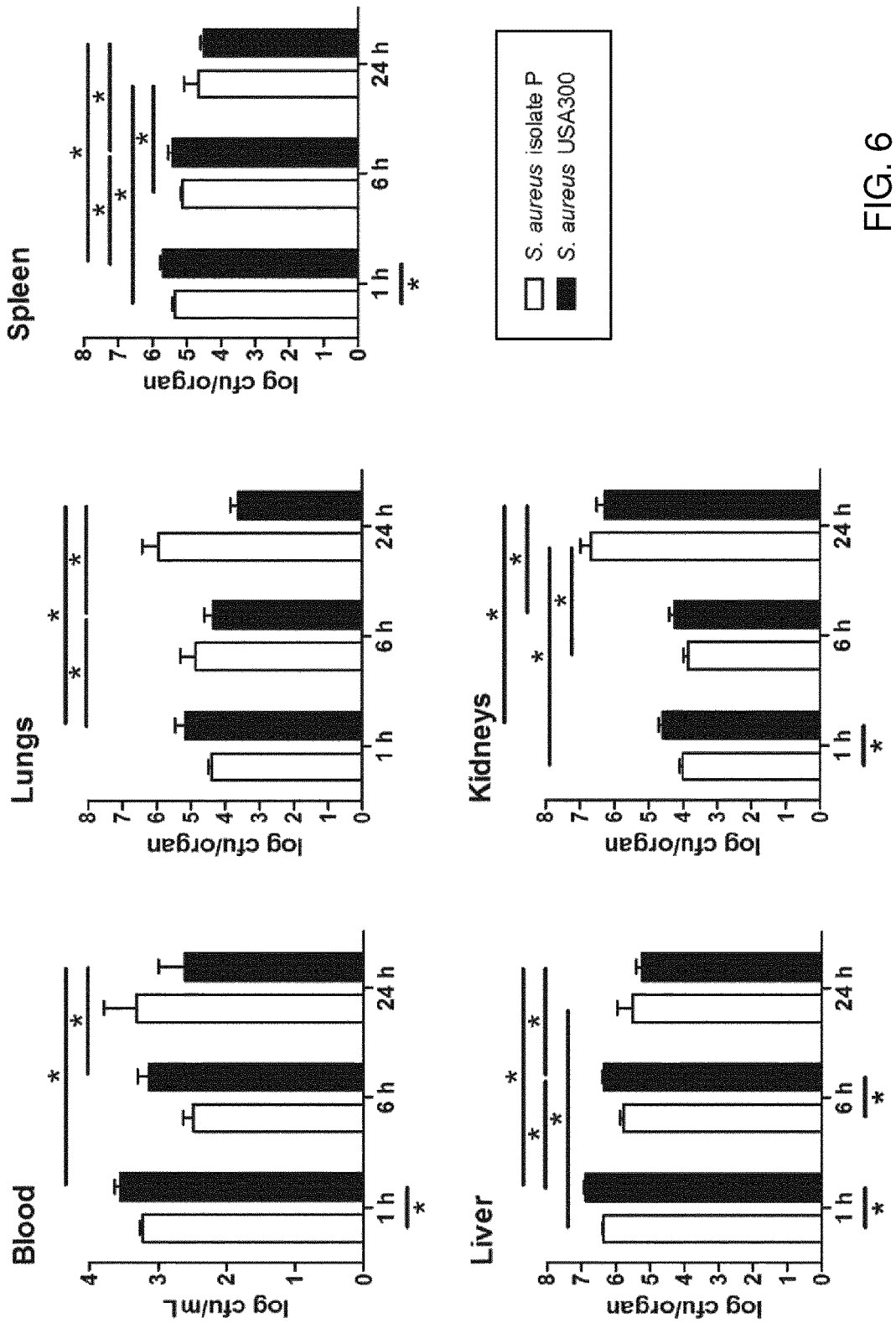

FIG. 6. *S. aureus* counts in blood and organs from mice with *S. aureus* bacteremia. Mice (4 per group) were infected with $2\text{-}4\times10^5$ cfu of *S. aureus* isolate P (open bars) or with $4\text{-}7\times10^5$ cfu of *S. aureus* USA300 (black bars), by intravenous inoculation, and were sacrificed at indicated time points. Quantitative cultures of blood and organs were performed. Results are expressed as mean with SD. Asterisks above the x-axis indicate statistically significant differences in cfu counts at the various time points (one-way ANOVA, P<0.05). Asterisks below the x-axis indicate statistically significant differences in cfu counts between mice with *S. aureus* isolate P bacteremia and mice with *S. aureus* USA300 bacteremia (t-test, P<0.003).

Figure 7:
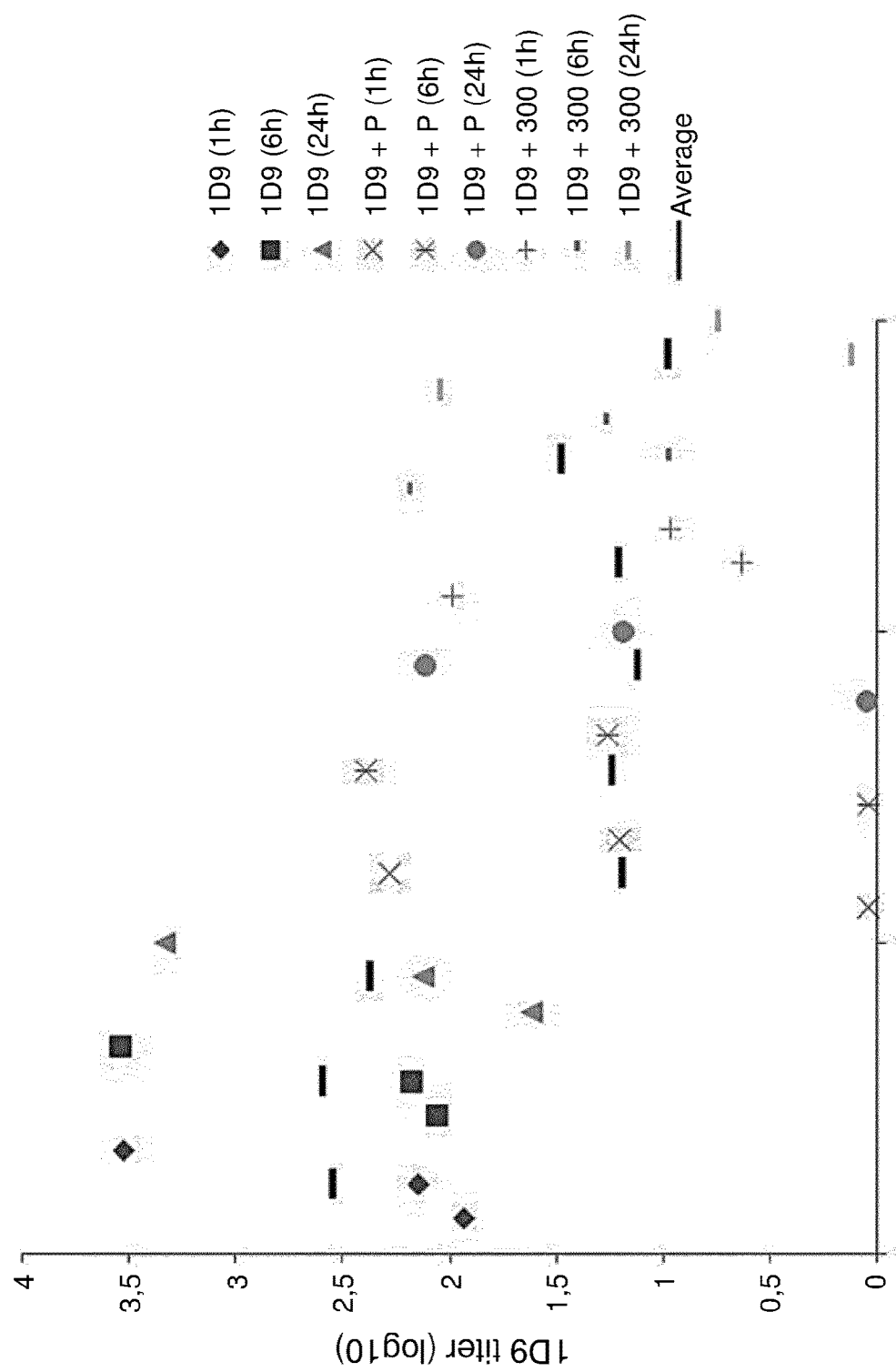

FIG. 7. Course of serum mAb 1D9 levels over time. Mice (n=3 per group) were treated intravenously with 5 mg/kg mAb 1D9. Three hours later, bacteremia was induced by either *S. aureus* isolate P (1D9+P) or *S. aureus* USA300 (1D9+300). Uninfected mice (1D9) were included as well. At indicated time points, serum levels of human mAb 1D9 were assessed using ELISA plates coated with 250 ng of purified IsaA per well. Mean serum levels are indicated by horizontal lines.

Figure 8:
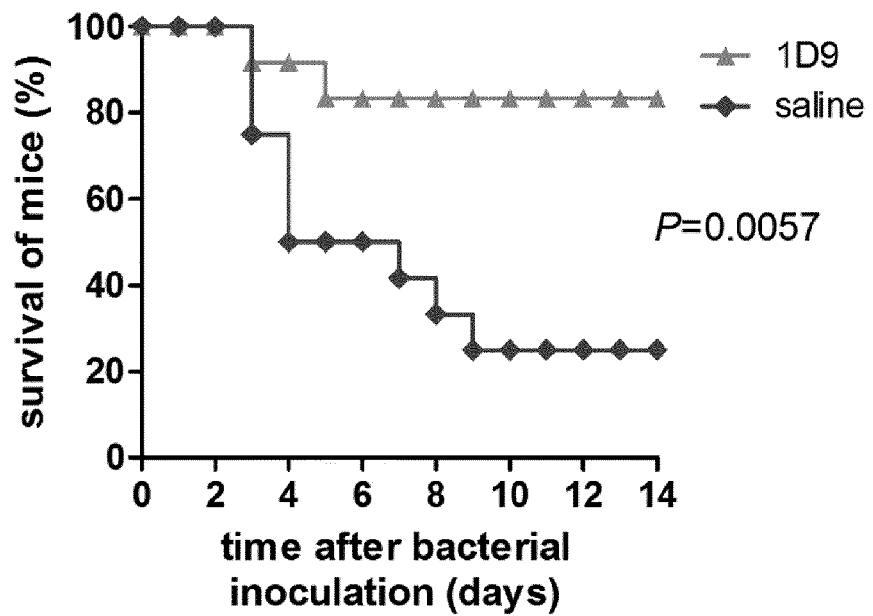

FIG. 8. Efficacy of a single dose of mAb 1D9 against *S. aureus* bacteremia. Mice (12 per group) were infected with $2\text{-}4\times10^5$ cfu of *S. aureus* isolate P by intravenous inoculation. Animals were treated intravenously with mAb 1D9 (5 mg/kg) or placebo (saline) 3 hours before infection Animal survival was monitored for 14 days. The significance of protection compared to that for animals receiving placebo was measured with the log rank test.

FIG. 9. IRDye 800CW labeled 1D9 binds to IsaA. Labeling of mAb 1D9 with IRDye 800CW was visualized by direct scanning at 800 nm of an LDS-PAA gel on which the labeled 1D9 had been separated (A) before gel staining, and (B) after Simply blue staining Different amounts (in μl) of IRDye 800CW labeled 1D9 were loaded as indicated, and BSA standards (4 μl loaded) of different concentrations were used. The molecular weight of marker proteins is indicated (in kDa). (C) The IRDye 800CW labeled 1D9 was found to bind IsaA with similar efficiency as unlabeled 1D9 (compare middle and lower panels), as evidenced both for purified IsaA (left panels) and IsaA expressed by *S. aureus* strain Newman (right panels). Binding of unlabeled 1D9 to IsaA was visualized with IRDye 800 goat anti-human IgG antibodies. Note that IsaA was detected both in cell fractions (P) and growth medium fractions (S) of *S. aureus* Newman. Importantly, binding of 1D9 to the IgG-binding protein A (Spa) and Sbi proteins was fully abolished in the *S. aureus* Newman ΔspaΔsbi strain, while IsaA binding was not affected in this strain. 1D9 did not bind to proteins of the *E. coli* and *B. subtilis* control strains.

FIG. 10. IRDye 800CW labeled HumAb 1D9 binds specifically to *S. aureus* cells. Aliquots from overnight cultures of the strains *S. aureus* Newman, Newman Δspa, Newman ΔspaΔsbi, *E. coli* DH5α and *B. subtilis* 168 were incubated with IRDye 800CW labeled 1D9 and spotted on Whatman paper (A) or glass slides (B). Subsequently, the paper and glass slides were scanned for fluorescent signal at 800 nm (A and the upper panel in B) as described in the materials and methods. The middle panel of B shows a non-fluorescent image of the same glass slides. The lower panels of B show cells of *S. aureus* Newman Δspa Δsbi (left) and *E. coli* (right) in the microphotographs of spots indicated with arrows in the middle panel of B. Dilution factors used are indicated on the left of each panel. Scale bar: 10 μm.

EXPERIMENTAL SECTION

The experimental section herein below describes the generation of a fully human monoclonal IgG1 antibody directed against the conserved *S. aureus* antigen IsaA. This mAb was generated using the CHR protocol (see ref. 18, 19) in which B lymphocytes were enriched for IsaA-binding B cells and subsequently cloned. Six nasal *S. aureus* carriers were selected as potential donors, in one of which B cells specific for IsaA were detectably present. One mAb that was produced from these B cells, 1D9, did bind to IsaA-His$_6$ and not to control antigens.

It is shown that this human mAb 1D9 binds to both IsaA-His$_6$ and native IsaA, as well as to a broad panel of 26 clinical *S. aureus* isolates, including MSSA and MRSA strains. *S. aureus* isolate P (MSSA) and *S. aureus* USA300 (MRSA) are among these strains, and binding of mAb 1D9 to these strains was excellent. Therefore, these strains are used for further experiments ex vivo and in vivo.

Materials and Methods

Bacteria.

The sequenced *S. aureus* strains Mu50, MW2, N315, COL, 8325-4, MRSA252, MSSA476, USA300 and Newman were used. The isogenic knock-out of Newman wild-type lacking protein A (Newman Δspa), the isogenic knock-out of Newman wild-type lacking both protein A and the second binding protein for immunoglobulins (Sbi) (Newman ΔspaΔsbi) (16), and the spa mutant of SH1000 (SH1000 Δspa) (17), were used as well. Moreover, 16 clinical *S. aureus* isolates (A, C, E-F, M-X), both MSSA and MRSA strains described by Ziebandt et al (7), were included. From these, *S. aureus* isolate P (MSSA) and *S. aureus* USA300 (MRSA) were used in the animal experiments.

To create the spa mutant of *S. aureus* SH1000, the kanamycin resistance marker encoded by pDG783 was introduced between the spa flanking regions via PCR with the primer pairs spa.fw ACCTGCTGCAAATGCTGCGC and spa.rev CTAATACGACTCACTATAGGGAGAGGT-TAGCACTTTGGCTTGGG. The obtained PCR fragment was ligated into pMAD (Arnaud et al. 2004. *Appl. Environ. Microbiol.* 70:6887-6891), and the resulting plasmid was used to transform competent *S. aureus* SH1000 cells. Blue colonies were selected on Tryptic Soy Agar (TSA) plates with erythromycin and kanamycin, and the spa mutant was subsequently identified following the previously described protocol (16).

Selection of Donors.

Healthy nasal *S. aureus* carriers were selected as potential donors for protective human antibodies. Therefore, the nasal *S. aureus* carrier state of healthy individuals was assessed by sampling the left and right anterior nares using transswabs (MWE, Corsham, England) as described earlier (14). The obtained samples were cultured on blood agar plates with 5% sheep blood. *S. aureus* identification was based upon colony morphology, Gram staining, catalase test and Pastorex Staph Plus test (Biorad, Veenendaal, The Netherlands).

Isolation and Immunodetection of IsaA.

The gene encoding IsaA was obtained by PCR using the primers IsaAHis.fw (AGGCACTCA<u>CCATGG</u>GAGCT GAAGTAAACGTTGATCAAG) and IsaAHis.rev (GTGAT-GTC<u>GAATTC</u>CGAATCCCCAAGCACCTAAACCTTG) and chromosomal DNA of *S. aureus* NCTC8325 as a template. For the cloning, the purified PCR product was digested with the restriction enzymes NcoI and HindIII (both underlined in the primer sequences) and ligated into these sites of plasmid pET24d (Novagen, Darmstadt, Germany) and transferred to electrocompetent *E. coli* BL21DE3 cells with selection on kanamycin. For protein expression, an overnight culture of *E. coli* BL21DE3 containing plasmid pET24dIsaA was diluted 1:100 in fresh Luria Bertani (LB) broth (Difco™, BD, Breda, The Netherlands). Four hours after induction of protein expression using 1 mM isopropyl-β-D-thiogalactopyranoside, cells were harvested and disrupted in binding buffer (with 6M urea) by making use of a French Pressure cell press (Thermo Scientific, Etten-Leur, The Netherlands) on ice. Cleared lysate of *E. coli* was mixed with His Mag Sepharose™ Ni magnetic beads (GE Healthcare, Diegem, Belgium) and prewashed with 3 volumes of binding buffer. The C-terminal his-tagged IsaA was eluted with 1 volume of binding buffer containing 500 mM imidazole. Fractions containing the purified IsaA-His$_6$ were pooled and dialyzed against phosphate buffered saline (PBS).

Cell and supernatant fractions from overnight cultures of *S. aureus* SH1000 Δspa were prepared as described before (16). Protein samples were separated using NuPAGE gels (Invitrogen™, Life Technologies, Bleiswijk, The Netherlands) according to the manufacturer's instructions and proteins were transferred to a Protran nitrocellulose membrane (Whatman, 's-Hertogenbosch, The Netherlands) by semi-dry blotting (75 min at 1 mA/cm$^2$). Membranes were incubated with specific rabbit antibodies against IsaA (kindly provided by N. Sakata(9)) or with the human mAb 1D9 (see below). After incubation with IRDye 800 goat anti-rabbit (IsaA) or IRDye 800 goat anti-human IgG antibodies respectively, the signals were detected using the Odyssey system (LI-COR Biosciences, Bad Homburg, Germany).

Production and Selection of Human Monoclonal Antibody.

Blood was drawn from nasal *S. aureus* carriers. The Independent Ethics Committee of the Foundation 'Evaluation of Ethics in Biomedical Research' approved the protocol for blood donation. The protocol is registered by QPS Groningen (code 04132-CS011). All volunteers provided their written informed consent.

Human monoclonal IgG1 antibodies were generated using the CHR protocol (molecular Cloning of the Human Response). Briefly, human peripheral blood cells were separated by Ficoll centrifugation and B lymphocytes were isolated using the EasySep Human B cell enrichment procedure (Stemcell technologies, Grenoble, France). Next, IsaA-specific memory B cells were enriched on a MoFlo cell sorter (DakoCytomation, Glostrup, Denmark) by selecting for biotinylated IsaA-His$_6$, CD27 and CD19. To this end, IsaA-His$_6$ was biotinylated in a carbonate buffer (pH 9.3) with excess Bioineamidocaproate N-hydroxysuccinimidyl ester, and subsequent dialysis against PBS. Selected B cells were incubated on CD40L-expressing 3T6-cells, and after 7 days the supernatant was tested for antibodies against IsaA. Positive wells were transferred on ELISPOT plates for 2 days. Cells were transferred back to 96-well plates in the presence of MegaCD40L (Enzo Life Sciences, Antwerpen, Belgium), and ELISPOT plates were analyzed for spots for IsaA. Finally, cells from ELISPOT-positive wells were single cell sorted and monoclonal antibodies (IgG1) were cloned as described (18, 19) with minor modifications. We purified mAbs using protein A agarose beads and finally tested them for binding to IsaA-His$_6$ by ELISA as described below. Finally, the IgG1 genes for the IsaA-specific monoclonal antibody 1D9 were sequenced and the translated sequence was compared to that of IgG1 sequences deposited in the NCBI database as shown.

Human mAbs directed against Protective Antigen (PA) of *Bacillus anthracis* (IQNPA) were described before (20) and used as an isotype control mAb.

Antigen ELISA.

High affinity 96-wells ELISA plates were coated with IsaA-His$_6$ (100 or 250 ng/well) or PA (100 ng/well), diluted in carbonate coating buffer (71 mM NaHCO$_3$, 29 mM Na$_2$CO$_3$, pH 9.6). Plates were blocked for 1 hour at 37° C. with blocking buffer (PBS containing 1% BSA). Purified plasma or antibodies were used in a titration range starting at 20 or 1000 ng/mL. Binding of antibodies was monitored by addition of goat anti-human-PO (1:7,500) or rabbit anti-human-HRP (1:5,000), diluted in conjugate buffer (PBS with 0.05% Tween-20 (PBST) and 5% fetal calf serum (FCS)) and incubated for 1 hour at 37° C. Between coating, blocking, sample incubation, conjugate incubation and color reaction, the wells were washed 3 times with PBST. After the conjugate incubation, the plates were incubated for 15 minutes in the dark at room temperature with TMB substrate (Kem-en-Tec Diagnostics, Taastrup, Denmark). The enzymatic reaction was stopped by using 0.2M H$_2$SO$_4$. The plates were read with the Magellan 2 program of the ELISA-reader, which was set on 450 nm absorbance and a reference filter of 620 nm. Samples were determined positive if the OD$_{450}$ was >3 times the OD$_{450}$ of PBS 1× (plasma of donors) or supernatant from B-cells cultivated in Linolea broth. To check if a positive signal was not the result of aspecific antibodies, the samples were also tested on a plate coated with 4% BSA instead of IsaA-His$_6$.

S. aureus Whole Cell ELISA.

Bacteria were grown overnight in HEPES buffered Iscove's Modified Dulbecco's Medium (IMDM without phenol red; Gibco®, Life Technologies, Bleiswijk, The Netherlands) and subsequently diluted in fresh medium to an OD$_{660}$ of 0.08. Bacteria were cultured until the mid-exponential (OD$_{660}$~0.5) growth phase, washed with PBS and stored at −20° C. Microlon ELISA plates (Greiner Bio-One, Alphen a/d Rijn, The Netherlands) were coated with 50 µL of bacteria per well at a density of 1×10$^8$ cfu/mL in PBS for 18 hours at 4° C. Plates were blocked with 4% BSA in PBST and washed 3 times with PBST. To block surface expressed IgG Fc-binding to protein A and Sbi of *S. aureus*, wells were incubated with 100 µg/mL normal guinea pig IgG (Jackson ImmunoResearch Laboratories, West Grove, Pa., USA) in PBST containing 1% BSA before addition of a serial dilution of biotinylated human mAbs. Bound IgG was detected with PO-labeled streptavidin (Dako, Heverlee, Belgium) and visualized using TMB as substrate. Reaction was stopped with 1M H$_2$SO$_4$ and plates were read at 450 nm.

Animals.

Specified pathogen-free (SPF) female BALB/cBYJ mice were obtained from Charles River (Saint-Germain-sur-l'Arbresle, France). Animals were 11-13 weeks old at the day of infection, and were given food and water ad libitum. The experimental protocols adhered to the rules specified in the Dutch Animal Experimentation Act (1977) and the published Guidelines on the Protection of Experimental Animals by the Council of the EC (1986). The Institutional Animal Care and Use Committee of the Erasmus University Medical Center Rotterdam approved the present protocols.

Effect of Monoclonal Antibody on *S. Aureus* Growth.

After overnight growth of bacteria in IMDM or Mueller Hinton Broth (MHB; Oxoid, Basingstoke, UK), cells were diluted 1:50 in fresh medium and mixed with an equal volume of buffer or human mAbs. Wells were loaded with 200 µL of this mixture, which was supplemented with 10% mouse serum, and incubated for 18 hours at 37° C. in a BioScreen C growth analyzer (Oy Growth Curves Ab Ltd, Helsinki, Finland) with shaking every 5 minutes. OD$_{600}$ was measured every 15 minutes.

Isolation of Neutrophils.

Human neutrophils were isolated from heparinized blood of healthy volunteers. Blood was 1:1 (v/v) diluted with PBS and loaded onto a gradient of Ficoll-Paque (density 1.077; GE Healthcare, Diegem, Belgium) and Histopaque (density 1.119; Sigma Aldrich, Zwijndrecht, The Netherlands). Neutrophils were recovered from the Histopaque layer and residual erythrocytes were lysed for 30 seconds with ice cold water. After restoration of isotonicity, cells were washed and resuspended in RPMI (Gibco®, Life Technologies, Bleiswijk, The Netherlands) containing 0.05% human serum albumin (HSA; Sanquin, Amsterdam, The Netherlands).

Mouse neutrophils were isolated from bone marrow of uninfected mice. Therefore, the femur and tibia of both hind legs were prepared, flushed with Hank's Balanced Salt Solution (HBSS; Gibco®, Life Technologies, Bleiswijk, The Netherlands) containing 0.1% HSA, 15 mM ethylenediaminetetraacetic acid (EDTA), and 25 mM HEPES, and residual erythrocytes were lysed with ice cold water. To enrich for neutrophils, cells were loaded onto a discontinuous Percoll (GE Healthcare, Diegem, Belgium) gradient of 81% and 62.5% and centrifuged for 30 minutes at 1500×g without brake. Cells were recovered from the band formed between the 62.5% and 81% layer, washed and resuspended in RPMI/HSA. Cell purity was determined by specific staining with phycoerythrin (PE)-labelled rat anti-Ly-6G (Gr-1) mAb (Invitrogen™, Life Technologies, Bleiswijk, The Netherlands) and flow cytometry (FACSCalibur; BD, Breda, The Netherlands) (purity 75-85%).

Quantitative Determination of Neutrophil Activation and Oxidative Burst.

The immune complex (IC) induced oxidative burst of isolated neutrophils was determined by luminol enhanced chemiluminescence. Therefore, white microplates (Cliniplate; Thermo Scientific, Etten-Leur, The Netherlands) were coated with 5 µg/mL HSA or IsaA-His$_6$ in 50 µL of 0.1 M carbonate buffer (pH 9.6) for 1 hour at 37° C. After washing with PBS, wells were blocked with 10% FCS and subsequently incubated with specific antibody in PBS/1% FCS, 1 µg/mL rabbit anti-HSA (Sigma Aldrich, Zwijndrecht, The Netherlands) or 3 µg/mL human mAb, for HSA and IsaA coatings, respectively. Control antibodies were normal rabbit IgG (Jackson ImmunoResearch Laboratories, West Grove, Pa., USA) and human IQNPA, respectively. After a final wash with PBS, 100 µl, HBSS with 0.1% HSA and 150 µM luminol was added and the plate was loaded into a CentroLB 960 microplate luminometer (Berthold Technologies, Vilvoorde, Belgium). The reaction was initiated by the addition of 50 µL neutrophils in HBSS/HSA at a concentration of $1.25 \times 10^6$ cells/mL for human and $5 \times 10^6$ cells/mL for mouse neutrophils, respectively. Oxidative burst was continuously recorded for 30 minutes at 37° C. and expressed as relative light units (RLU). Alternatively, the area under the curve was calculated for each sample.

Phagocytosis Assay.

S. aureus clinical isolate P and S. aureus USA300 were labeled with 100 µg/mL fluorescein isothiocyanate (FITC) for 1 hour at 4° C., washed with RPMI/HSA and stored at −20° C. In wells of a round-bottom microplate, bacteria were opsonized with a serial dilution of normal human pooled serum (HPS), normal mouse pooled serum (MPS), complement inactivated serum (heated for 30 minutes at 56° C.), or a combination of serum and human mAbs. After 15 minutes at 37° C., human or mouse neutrophils were added at a cell to bacteria ratio of 1:10 in a final volume of 50 µL. Phagocytosis was allowed for 15 or 30 minutes at 37° C. on a shaking plateau (700 rpm) for human and mouse neutrophils, respectively. Reaction was stopped by the addition of ice cold paraformaldehyde to a final concentration of 1%. Samples were analyzed on a flow cytometer (FACSCalibur; BD, Breda, The Netherlands) and the mean fluorescence of properly gated neutrophils was determined.

IsaA Expression by S. aureus Isolate P and S. aureus USA300.

For detection of IsaA expression by S. aureus isolate P and S. aureus USA300, both strains were grown in Brain Heart Infusion broth (BHI; BD, Breda, The Netherlands) and stored as described in the section 'S. aureus whole cell ELISA'. Around $10^5$ cfu of bacteria were inoculated BHI, IMDM, or serum of BALB/cBYJ mice (Charles River, Saint-Germain-sur-l'Arbresle, France). Culture samples were taken 6 and 24 hours after inoculation. For colony counting, diluted and undiluted suspensions were plated on blood agar with 5% sheep blood. After overnight incubation at 35° C. colonies were counted. For Western analysis, cell and supernatant fractions were prepared and analyzed by immunodetection as described in the section 'Isolation and immunodetection of IsaA'.

Infection Model of S. aureus Bacteremia.

S. aureus isolate P was grown overnight at 35° C. on blood agar plates with 5% sheep blood. Cultures of S. aureus, grown in BHI until $OD_{560} \sim 1.0$, were stored at −80° C.

For infection, a suspension of staphylococci was defrosted and centrifuged for 10 minutes at 14,000×g. The S. aureus pellet was resuspended in saline, and diluted to $2-4 \times 10^6$ cfu/mL of S. aureus isolate P. To establish bacteremia, 100 µL of S. aureus was injected into the tail vein. Clinical signs of illness in each mouse were evaluated twice daily. Mice with bad fur were scored −2. Mice with bad fur and hunched back were scored −3. Mice with bad fur and hunched back and that were instable were scored −4. These mice showed severe signs of illness and were euthanized by $CO_2$ exposure. Euthanized mice were considered as deaths, as pilot experiments showed that mice with severe signs of illness die before the next time point.

For assessment of the efficacy of human mAb in protection against death, mice were treated intravenously with either human mAb (5 mg/kg in a volume of 100 µL) or saline (n=12 per group). Three hours before treatment, S. aureus bacteremia was induced. Animal survival rate over 14 days after infection was monitored.

For characterization of the early course of bacteremia, the bacterial load in blood and infected organs was assessed at various intervals after infection. Mice (n=4 per time point) were sacrificed at 1, 6, or 24 hours by $CO_2$ exposure. A blood sample was taken via (transcutaneous) cardiac puncture and collected in a vial containing Lithium Heparin (Sarstedt, Etten-Leur, The Netherlands). The lungs, spleen, liver, and kidneys were removed aseptically and homogenized (Polytron, Kinematica, Luzern, Switzerland) in 2 mL of saline for 10 seconds at 30,000 rpm at room temperature. Undiluted homogenate suspensions and blood and 10-fold serial dilutions of homogenates and blood in saline were plated on blood agar with 5% sheep blood. After overnight incubation at 35° C. colonies were counted.

For determination of human mAb serum levels over time, mice were treated intravenously with human mAb (5 mg/kg in a volume of 100 µL). Three hours after treatment, bacteremia was induced by either S. aureus isolate P or S. aureus USA300 (n=3 per group). Uninfected mice were included as well. Blood was withdrawn from the tail artery of infected mice at 1, 6, and 24 hours after infection and collected in a Microvette® CB300 capillary tube (Sarstedt, Etten-Leur, The Netherlands). Sera were prepared and stored at −80° C. Serum levels of human mAb were determined by antigen ELISA as described above.

Statistical Analysis.

For comparison of cfu counts in blood and organs of infected mice, cfu counts were $log_{10}$ transformed before analysis. Mean cfu counts at 1, 6, and 24 hours were compared using one-way ANOVA (IBM SPSS Statistics version 20, IBM Corporation, Armonk, N.Y.). T-test was used for comparison of cfu counts in mice with S. aureus isolate P bacteremia and mice with S. aureus USA300 bacteremia (IBM SPSS Statistics version 20; IBM Corporation, Armonk, N.Y., USA). Log rank test was used to determine statistical differences in animal survival rate between groups (GraphPad Prism 5 for Windows; GraphPad Software Inc., La Jolla, Calif., USA). Differences were considered statistically significant when 2-sides P-values were <0.05. As multiple comparisons were made with the t-test, a Bonferroni correction was applied. P-values<0.003 were considered statistically significant.

Example 1: Selection of Donors and Generation of Antibodies

Figure 2B:
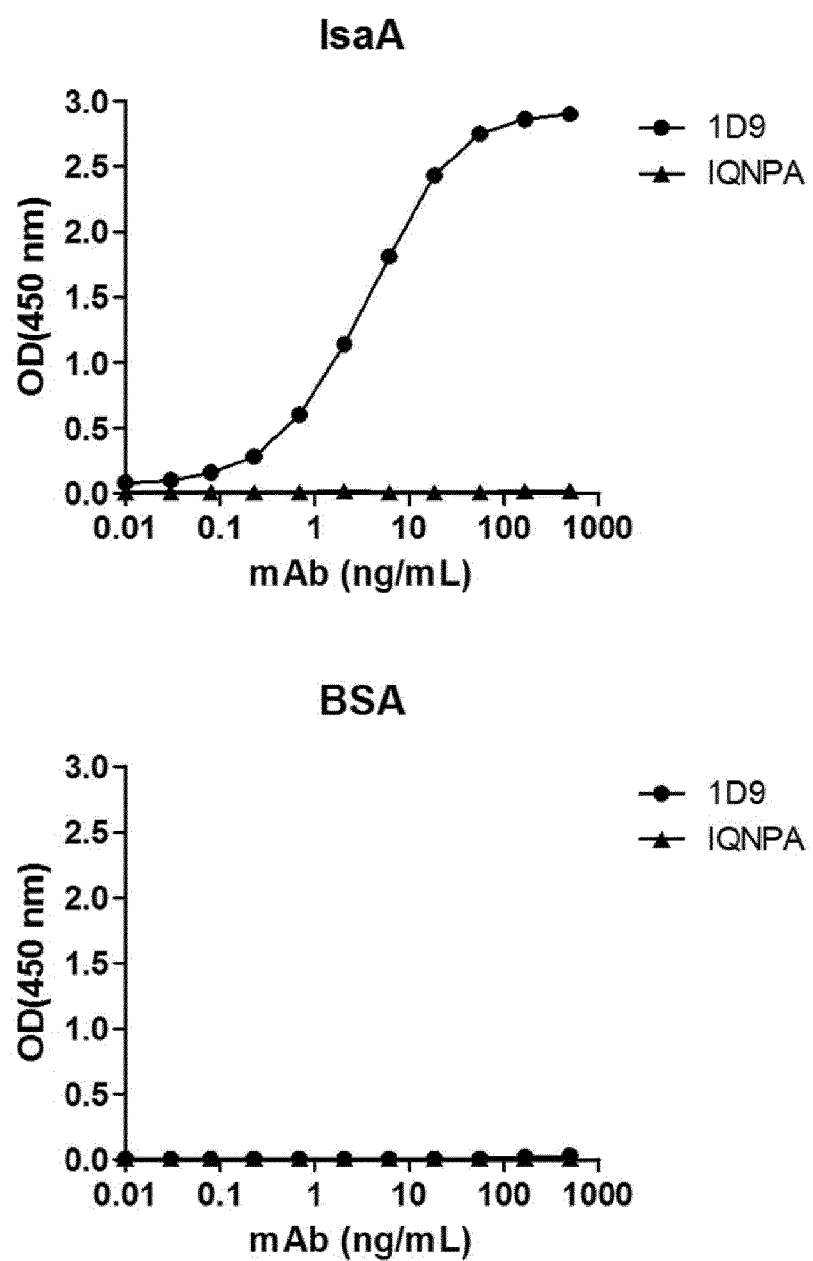
Figure 2C:
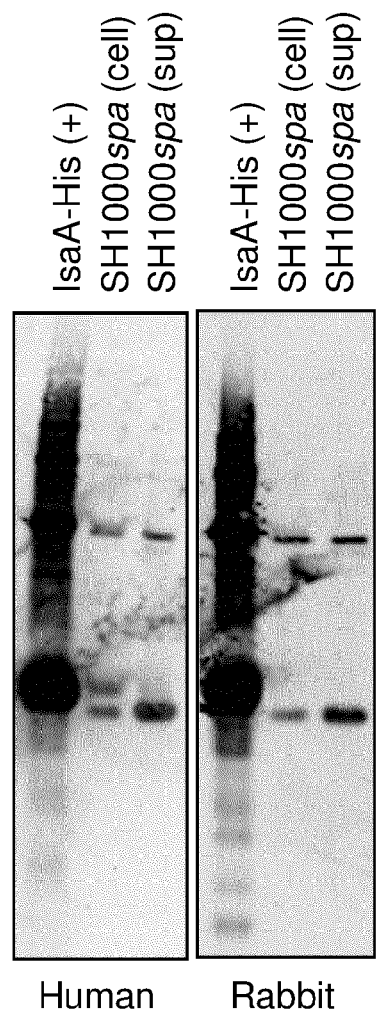

Using nasal swab analyses, six volunteers were identified as S. aureus carriers. FIG. 2A shows that five out of six nasal carriers had significant IgG levels for IsaA. Donor T7-1 was positive for non-staphylococcal control antigens (PA and BSA) as well. Material from this donor was not used to prevent collection of high-binding non-specific antibodies. Blood from the four donors who had IgG against IsaA and not against the control antigens was tested for the presence of monoclonal B cells specific for IsaA. Donor T7-5 was identified as being positive for antibody-producing B cells specific for IsaA as determined by ELISPOT after selection of IsaA-binding B lymphocytes. Human mAbs were generated, and six of these were found to be positive for binding to IsaA-$His_6$. Five of these were positive for the control antigens as well. One monoclonal ("1D9") was positive for IsaA-$His_6$ and negative for control antigens (FIG. 2B). This human mAb bound to native IsaA as well, as shown by Western blot analysis (FIG. 2C). Both mAb 1D9 and rabbit polyclonal anti-IsaA bound cellular and supernatant protein extract of S. aureus SH1000 Δspa.

Example 2: Binding of mAb 1D9 to S. aureus

Figure 2D:
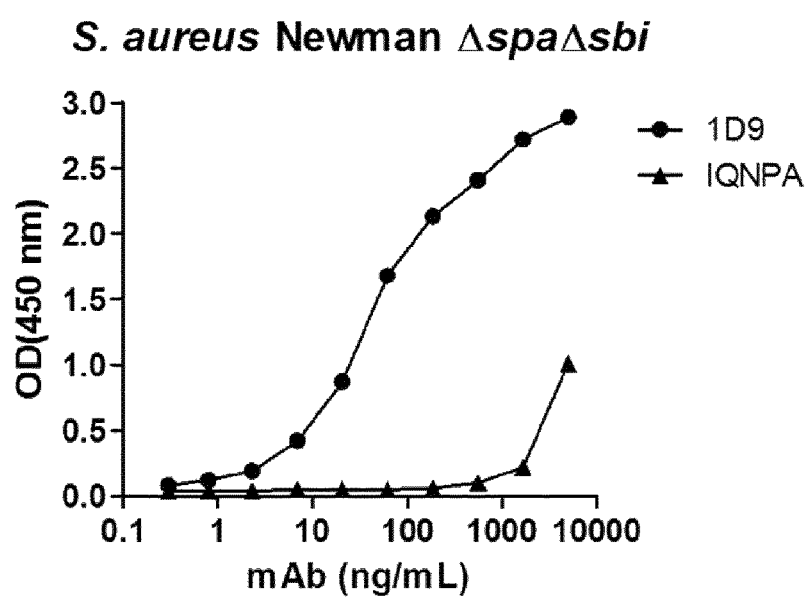
Figure 3A:
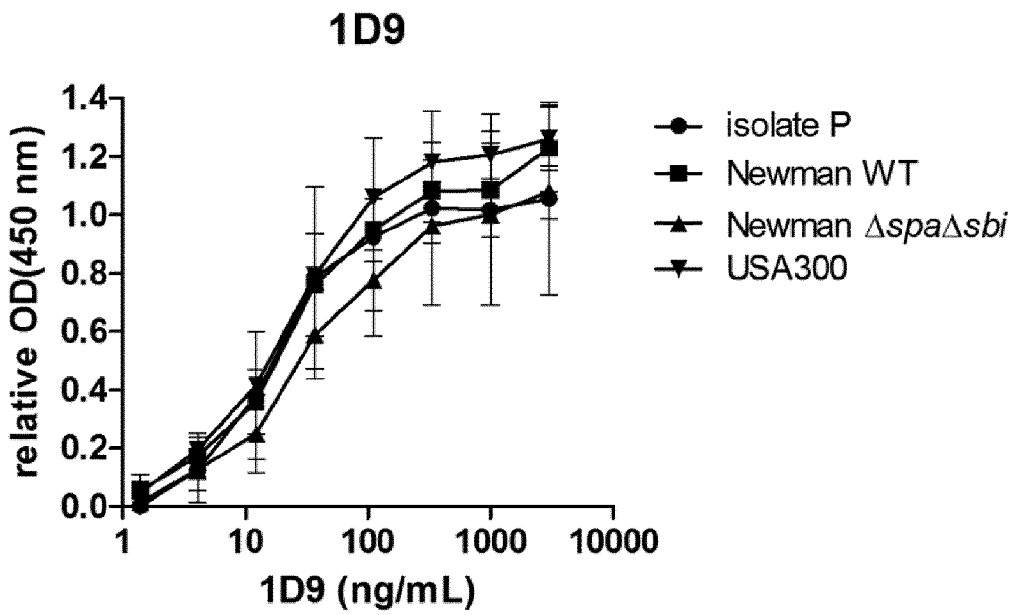
Figure 3B:
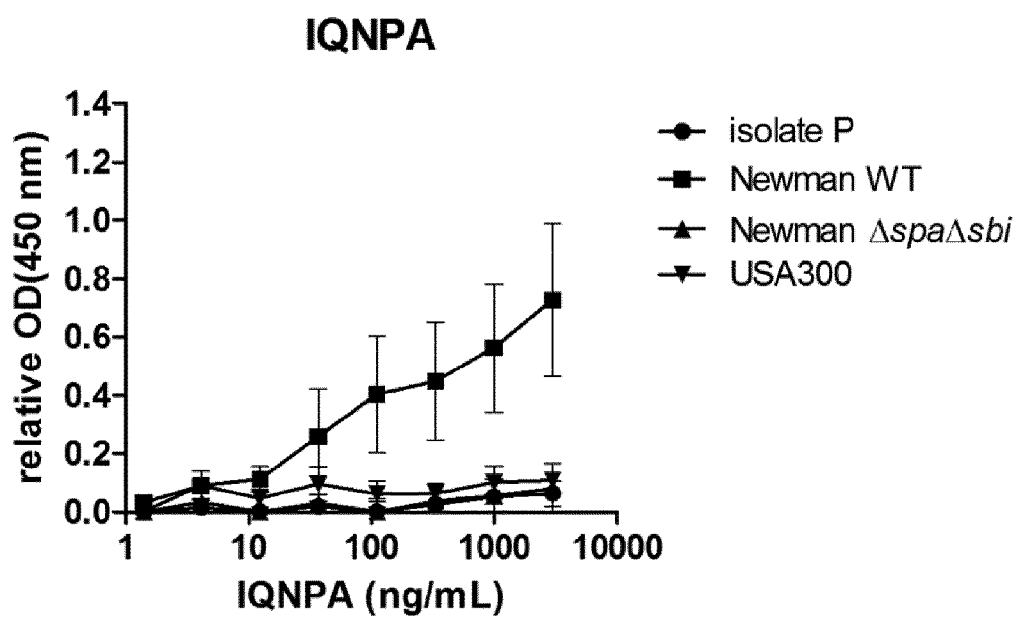
Figure 3C:
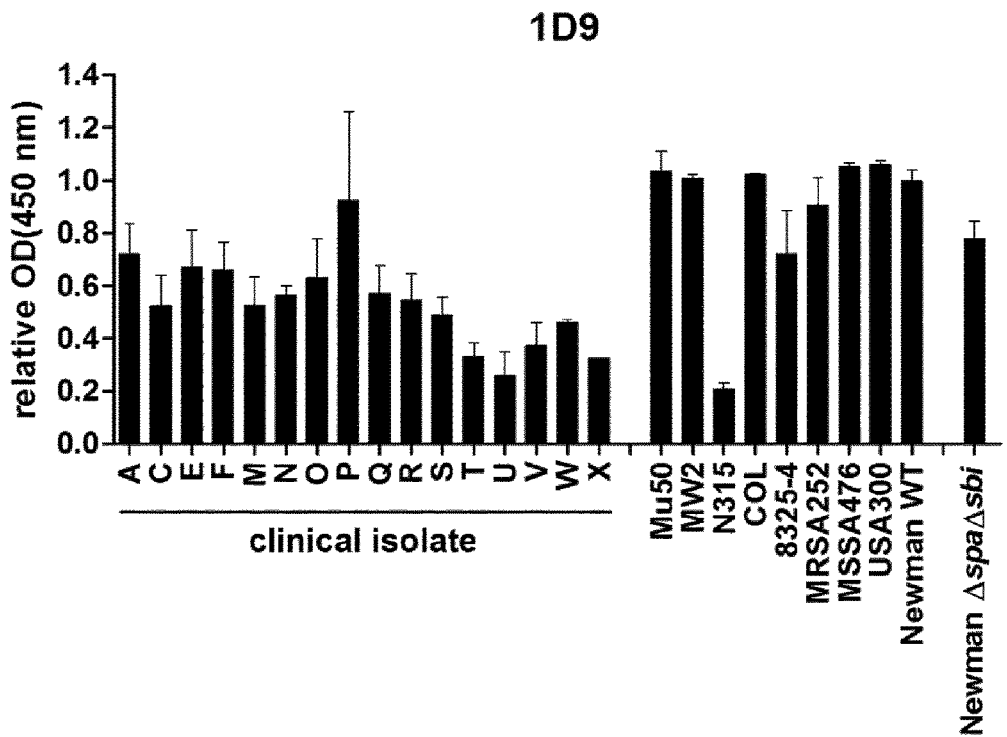
Figure 3D:
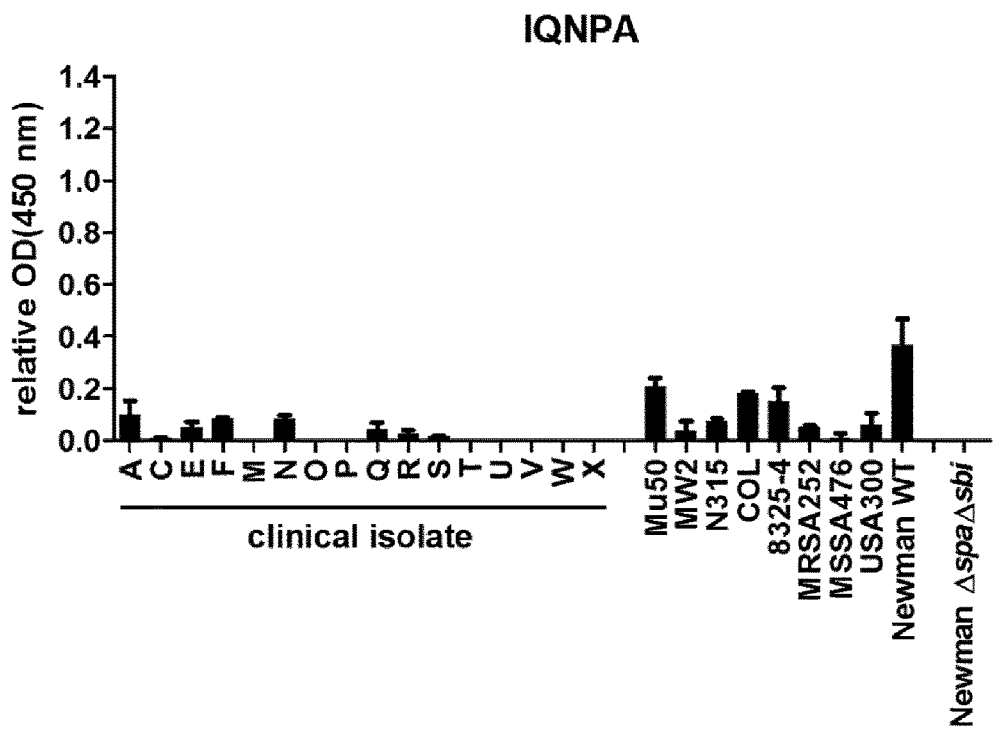
Figure 4A:
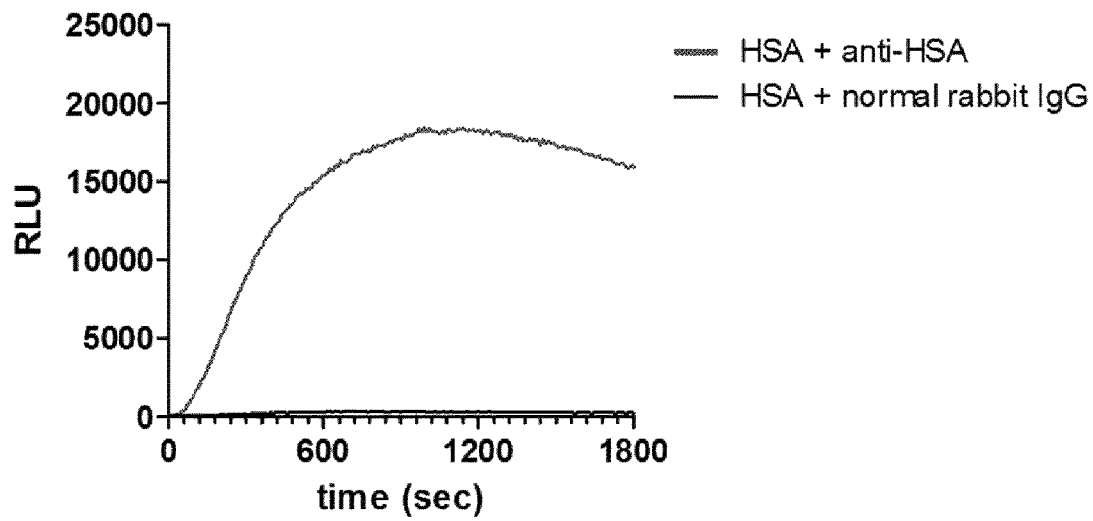
Figure 4B:
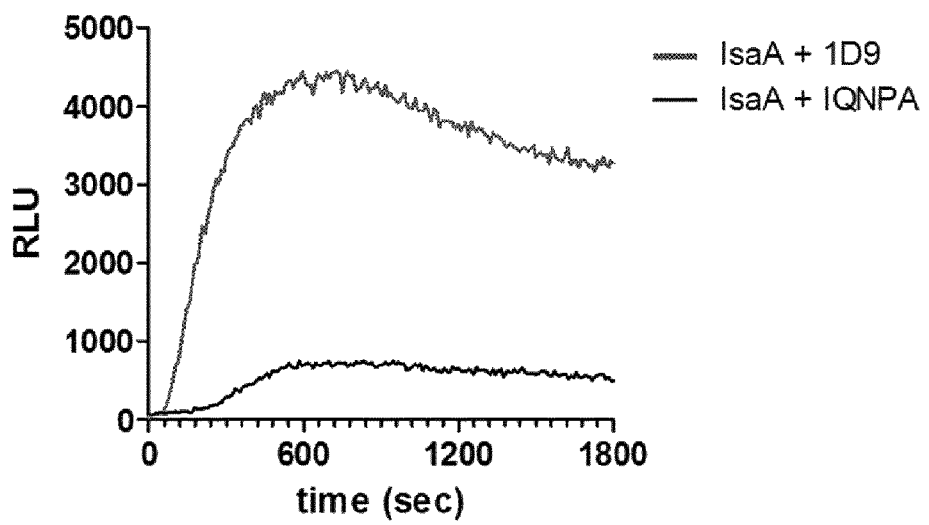
Figure 4C:
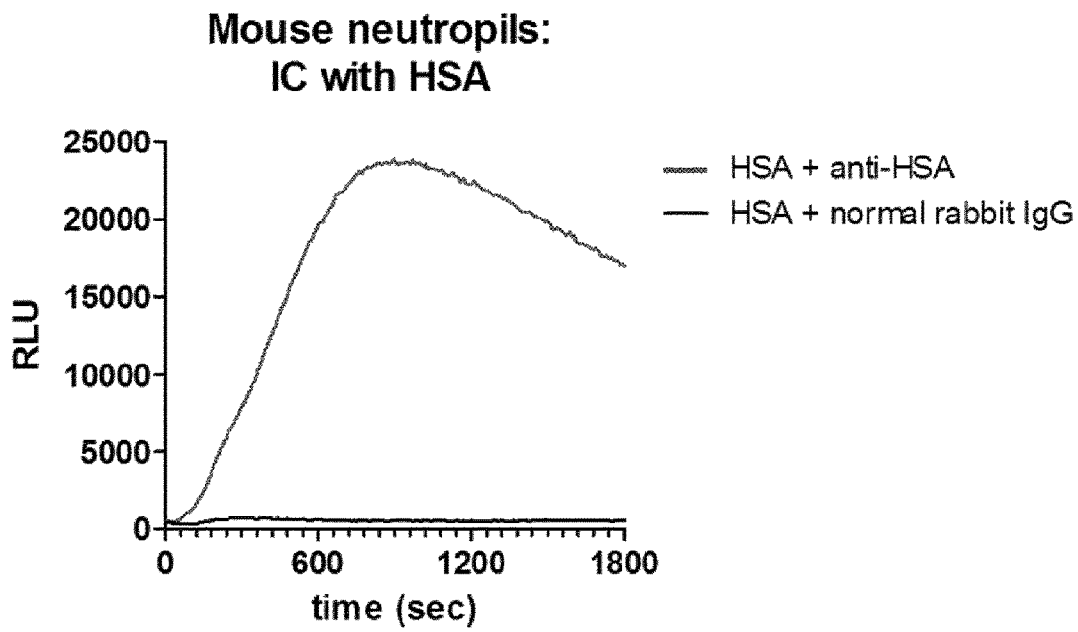
Figure 4D:
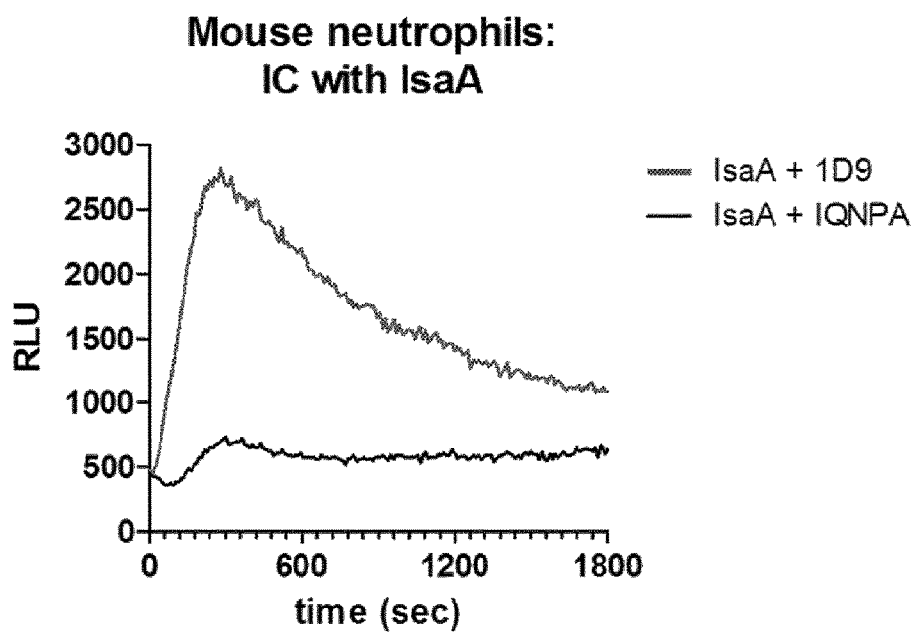

After the generation of the human mAb 1D9, which is highly specific for IsaA, we assessed whether this mAb was able to bind to whole cell S. aureus as well. First, binding of mAb 1D9 to S. aureus Newman ΔspaΔsbi was tested (FIG. 2D). As this S. aureus strain lacks protein A and Sbi, which are able to bind to the Fc region of immunoglobulins, aspecific binding of mAb 1D9 to protein A and Sbi can be ruled out. mAb 1D9 bound to this staphylococcal strain with high affinity and strength.

Next, we assessed whether the human mAb 1D9 bound to whole cells of various S. aureus strains with the antibody binding proteins protein A and Sbi. Binding of mAb 1D9 to S. aureus Newman ΔspaΔsbi, nine sequenced S. aureus strains and 16 clinical S. aureus isolates, including both MSSA and MRSA strains, was assessed. The human mAb 1D9 bound well to all MSSA strains, among which S. aureus isolate P, and to all MRSA strains, among which S. aureus USA300 (FIG. 3). Binding of the control human IgG1 IQNPA to the bacteria was observed until 0.1 μg/mL despite blocking surface expressed IgG Fc-binding proteins with a non-related guinea pig IgG. Therefore, binding of mAb 1D9 above 0.1 μg/mL cannot always be considered IsaA specific, except for the strain Newman ΔspaΔsbi. Of note is the variability of control human mAb IQNPA binding, possibly reflecting variation in surface expressed protein A and/or Sbi of the various strains.

Example 3: Activation of Human or Mouse Neutrophils by mAb 1D9

To explore the potential Fcγ receptor (FcγR) stimulation of human mAb 1D9 for both human and mouse cells, isolated neutrophils were challenged with IsaA-1D9 IC to generate an oxidative burst. The luminol enhanced chemiluminescence was properly initiated with both control IC consisting of HSA/rabbit anti-HSA IgG as well as IC consisting of IsaA-1D9 (FIG. 4, Table 2). Omission of either antigen or specific IgG or exchange with isotype control IgG did not activate the oxidative burst. This indicates a specific interaction of IC, containing rabbit or human IgG, with both the human and mouse FcγRs expressed on the surface of the neutrophils.

TABLE 2

Activation of human and mouse neutrophils by mAb 1D9.

| | AUC ($*10^6$) | | | |
| | human neutrophils | | mouse neutrophils | |
| condition | mean | SD | mean | SD |
|---|---|---|---|---|
| buffer | 0.41 | 0.25 | 0.52 | 0.31 |
| HSA + buffer | 2.39 | 4.72 | 0.59 | 0.43 |
| HSA + normal rabbit IgG | 2.78 | 5.16 | 0.66 | 0.44 |
| HSA + anti-HSA | 16.25 | 9.08 | 17.84 | 15.86 |
| buffer | 0.48 | 0.28 | 0.43 | 0.30 |

TABLE 2-continued

Activation of human and mouse neutrophils by mAb 1D9.

| | AUC ($*10^6$) | | | |
| | human neutrophils | | mouse neutrophils | |
| condition | mean | SD | mean | SD |
|---|---|---|---|---|
| IsaA + buffer | 0.65 | 0.44 | 0.54 | 0.46 |
| IsaA + IQNPA | 0.73 | 0.54 | 0.54 | 0.48 |
| IsaA + 1D9 | 4.30 | 3.25 | 2.03 | 1.24 |

Plates were coated with 5 μg/mL HSA or IsaA, blocked with 10% fetal calf serum and incubated with 1 or 3 μg/mL rabbit anti-HSA or mAb 1D9, respectively. Control antibodies were normal rabbit IgG or human control mAb IQNPA. Neutrophils (human neutrophils $1.25 \times 10^6$ cells/mL, mouse neutrophils $5 \times 10^6$ cells/mL) were added to initiate the reaction. Oxidative burst was measured for 30 minutes at 37° C. Area under the RLU-time curve is shown.

Example 4: IsaA Expression by S. aureus Isolate P and S. aureus USA300

To estimate the production of IsaA by S. aureus isolate P and S. aureus USA300 in different media and at different stages of growth, both strains were grown in the chemically defined media BHI and IMDM, as well as in pooled serum from BALB/c mice. After exponential and overnight growth in BHI or IMDM, no clear differences in expression and secretion were detected in a Western blot analysis (data not shown). As shown in FIG. 5, the expression of IsaA was more or less identical during growth in IMDM or mouse serum. A protein A band, due to a specific binding of IgG, was observed as a background signal. Interestingly, after 24 hours of growth in mouse serum, a much higher expression of protein A was observed in S. aureus USA300 than in S. aureus isolate P.

Example 5: Distribution of S. aureus in Blood and Infected Organs

To study the fate of S. aureus inoculated in the blood and the early course of S. aureus isolate P and S. aureus USA300 bacteremia, infected mice were sacrificed at various time points, and the bacterial load in blood and infected organs was determined (FIG. 6). In both mice with S. aureus isolate P bacteremia and mice with S. aureus USA300 bacteremia, ~99% of staphylococci had disappeared from the blood already 1 hour after infection. In mice with S. aureus isolate P bacteremia, the bacterial load in spleen and liver decreased within the first 24 hours after infection. In contrast, the number of S. aureus in the kidneys increased over this time period. In mice with S. aureus USA300 bacteremia, the bacterial load in blood, lungs, spleen, and liver decreased between 1 hour and 24 hours after infection, while in kidneys an increase of the S. aureus load was observed. When staphylococcal load in mice with S. aureus isolate P bacteremia and in mice with S. aureus USA300 bacteremia was compared, the bacterial load in blood, spleen, liver, and kidneys was elevated after 1 hour in mice with S. aureus USA300 bacteremia. After this time point, these differences disappeared, except for the liver, in which the bacterial load at 6 hours was elevated in mice with S. aureus USA300 bacteremia as well.

Example 6: Course of Serum mAb 1D9 Levels Over Time

Levels of human mAb 1D9 in uninfected mice as well as in mice with S. aureus bacteremia were monitored in the first period after injection (FIG. 7). The estimated concentration of human mAb 1D9 direct after intravenous injection was ~135 μg/mL of serum. Within the first hour after injection, a major part of this mAb was no longer detectable in serum, as the concentrations dropped to 0.3 to 30 µg/mL of serum. However, these levels remained stable in the first 24 hours. In infected mice, the mean mAb 1D9 titers showed a log reduction compared to uninfected mice. No differences in mAb 1D9 titers were observed between mice with either *S. aureus* isolate P or *S. aureus* USA300 bacteremia.

Example 7: Protective Effect of mAb 1D9 in Mice with *S. aureus* Bacteremia

The in vivo efficacy of mAb 1D9 was assessed in a *S. aureus* bacteremia model in mice. Bacteremia was induced by *S. aureus* isolate P, a clinical MSSA sepsis isolate. To test whether treatment with mAb 1D9 protects against death due to *S. aureus* bacteremia, mice were treated intravenously with mAb 1D9 or a placebo. Saline was used as placebo treatment, as pilot experiments showed that animal survival of saline-treated mice was comparable to that of mice treated with the isotype control human mAb IQNPA (5 mg/kg, data not shown).

Animal survival of placebo-treated mice declined gradually over 14 days, resulting in 25-42% of mice that survived the study period. After this time point, no changes in animal survival were observed.

Prophylactic treatment with 5 mg/kg mAb 1D9, at 3 hours before infection, resulted in increased time to death and significantly improved survival rate of mice infected with *S. aureus* isolate P (83% animal survival; P=0.0057; FIG. 8).

Example 8: Diagnostic Application of Antibody 1D9

Bacterial strains, plasmids and growth conditions.

Strains used in this study are listed in Table 3. Strains of *S. aureus* were grown in tryptic soy broth (TSB, OXOID) and supplemented with 20 µg/ml of kanamycin for *S. aureus* Newman Δspa, Δsbi. *E. coli* and *B. subtilis* were grown in Luria broth (LB). All strains were grown at 37° C. with shaking (250 rpm).

TABLE 3

Bacterial strains used

| Strains | Relevant phenotype(s) or genotype(s) | Source or reference |
|---|---|---|
| *E. coli* DH5α | λ⁻ φ80dlacZΔM15 Δ(lacZYA-argF)U169 recA1 endA hsdR17(⁻k⁻ ᵐk⁻)supE44 thi-1 gyrA relA1 | Novagen, Madison WI, USA |
| *B. subtilis* 168 | trpC2 | Kunst et al., 1997 |
| *S. aureus* Newman | NCTC 8178 clinical isolate | Duthie and Lorenz, 1952 |
| *S. aureus* Newman Δspa | spa mutant | Patel et al., 1987 |
| *S. aureus* Newman ΔspaΔsbi | spa sbi mutant | Sibbald et al., 2010 |

Labeling of Monoclonal Antibody 1D9.

The human monoclonal antibody 1D9 directed against the *S. aureus* secreted protein IsaA (31) was labeled as follows: 200 µl of HumAb 1D9 (1.15 mg/ml) in PBS was adjusted to pH 8.5 by adding 1M K₂HPO₄ (pH 9) and mixed with 0.5 µl IRDye 800CW in DMSO (5 mg/ml, LI-COR Biosciences, Bad Homburg, Germany) and incubated at room temperature for 2 hours while being protected from light. After incubation, the mix was desalted using a PD minitrap G-25 desalting column (GE Healthcare, Germany) following the manufacturer's instructions. The eluted labeled antibody was stored at 4° C. and protected from light. Proper labeling was confirmed by separating different amounts of IRDye 800CW labeled HumAb 1D9 in a LDS-PAA gel (NuPAGE gels, Life Technologies, Bleiswijk, The Netherlands) according to the manufacturer's instructions, together with unlabeled BSA standards (Sigma, St. Louis Mo., USA), and visualized with a LI-COR Odyssey scanner (LI-COR Biosciences). After protein staining (Simply blue safe stain, Life Technologies), images of the gel were captured with the Gbox Chemie XT 16 (Syngene, UK) from which antibody concentration was estimated. Antigen specificity of the IRDye 800CW labeled HumAb 1D9 was assessed as follows. Different samples of IsaA purified as described previously (31), and cell and supernatant fractions from overnight cultures of *S. aureus* Newman, *S. aureus* Newman Δspa, *S. aureus* Newman Δspa Δsbi, *E. coli* and *B. subtilis* were prepared as described before (16, 31), separated using NuPAGE gels (Life Technologies) and proteins were transferred to a Protran nitrocellulose membrane (Whatman, 's-Hertogenbosch, The Netherlands) by semi-dry blotting. Membranes were incubated with either HumAb 1D9, followed by incubation with IRDye 800 goat anti-human IgG antibodies, or IRDye 800CW labeled HumAb 1D9. Signals were detected using the Odyssey scanner (LI-COR Biosciences).

Staining and Detection of Bacteria with Labeled Monoclonal Antibody 1D9.

Overnight cultures were diluted into 1 ml PBS to an optical density of 1 (600 nm), washed once with 1 ml PBS, and resuspended in 100 µl PBS with IRDye 800CW labeled HumAb 1D9 (2 µg/ml) or without 1D9 for immunoblot analysis. After 5 min. incubation cells were washed 3× with 1 ml PBS, and resuspended in 100 µl of PBS, from which additional 1:5 serial dilutions were made. Two microliters of each undiluted and diluted resuspensions were spotted onto Whatman chromatography paper (GE Healthcare). Spots were visualized with the Odyssey scanner (LI-COR Biosciences). Additionally, 2 µl of undiluted resuspensions were spotted onto glass slides (Polysine slides, Thermo Scientific, Germany) and pictures were taken with a 100×PL Fluotar lens using a Leica DMI 6000B microscope, and with the Odyssey scanner (LI-COR Biosciences). Immunoblots of cell and supernatant fractions from cultures resuspended in PBS without labeled 1D9 were processed as indicated before, incubated with labeled 1D9, and signals were detected using the Odyssey scanner (LI-COR Biosciences).

Results

Labeled 1D9 Binds Specifically to IsaA.

Figure 9A:
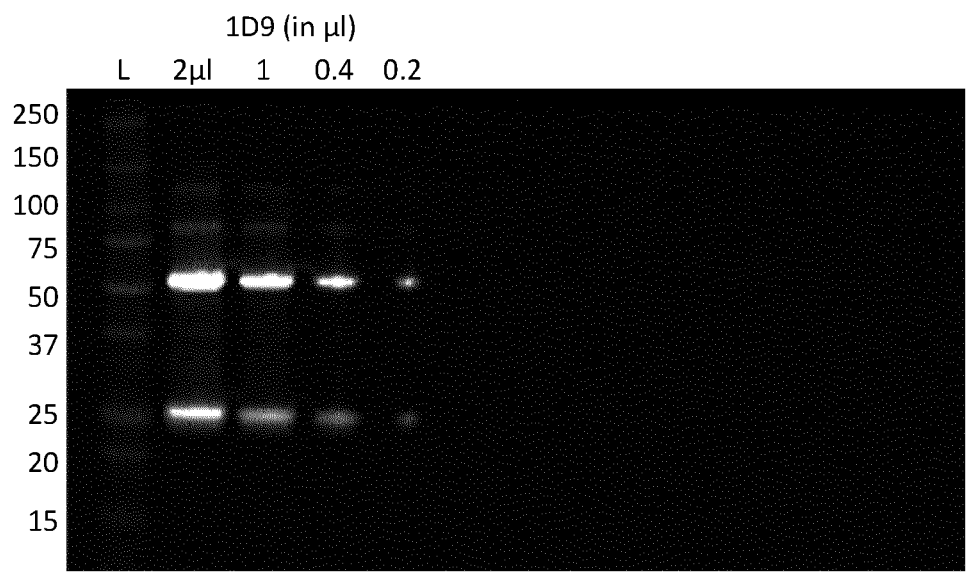
Figure 9B:
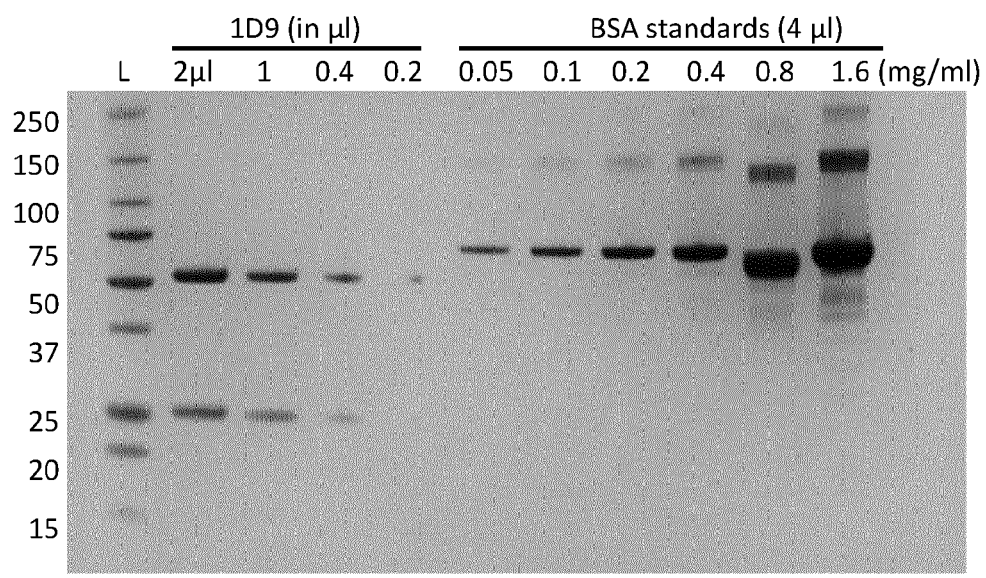

In a recent publication we described the isolation and production of the HumAb 1D9, which is directed against the *S. aureus* protein IsaA (31). To investigate the possibility of using this antibody for the in vitro and in vivo detection of *S. aureus* cells, HumAb 1D9 was randomly labeled with the infrared fluorescent dye IRDye 800CW. The effective labeling of HumAb 1D9 was confirmed by directly detecting fluorescence of the antibody after separation by LDS PAGE (FIG. 9A). The antibody concentration (0.4 mg/ml) was estimated by simultaneously separating a BSA standard dilution series on the same gel and subsequent Simply blue safe staining (FIG. 9B). BSA standards were unlabeled and therefore they are only detectable upon Simply blue safe staining as shown in FIG. 9B.

Figure 9C:
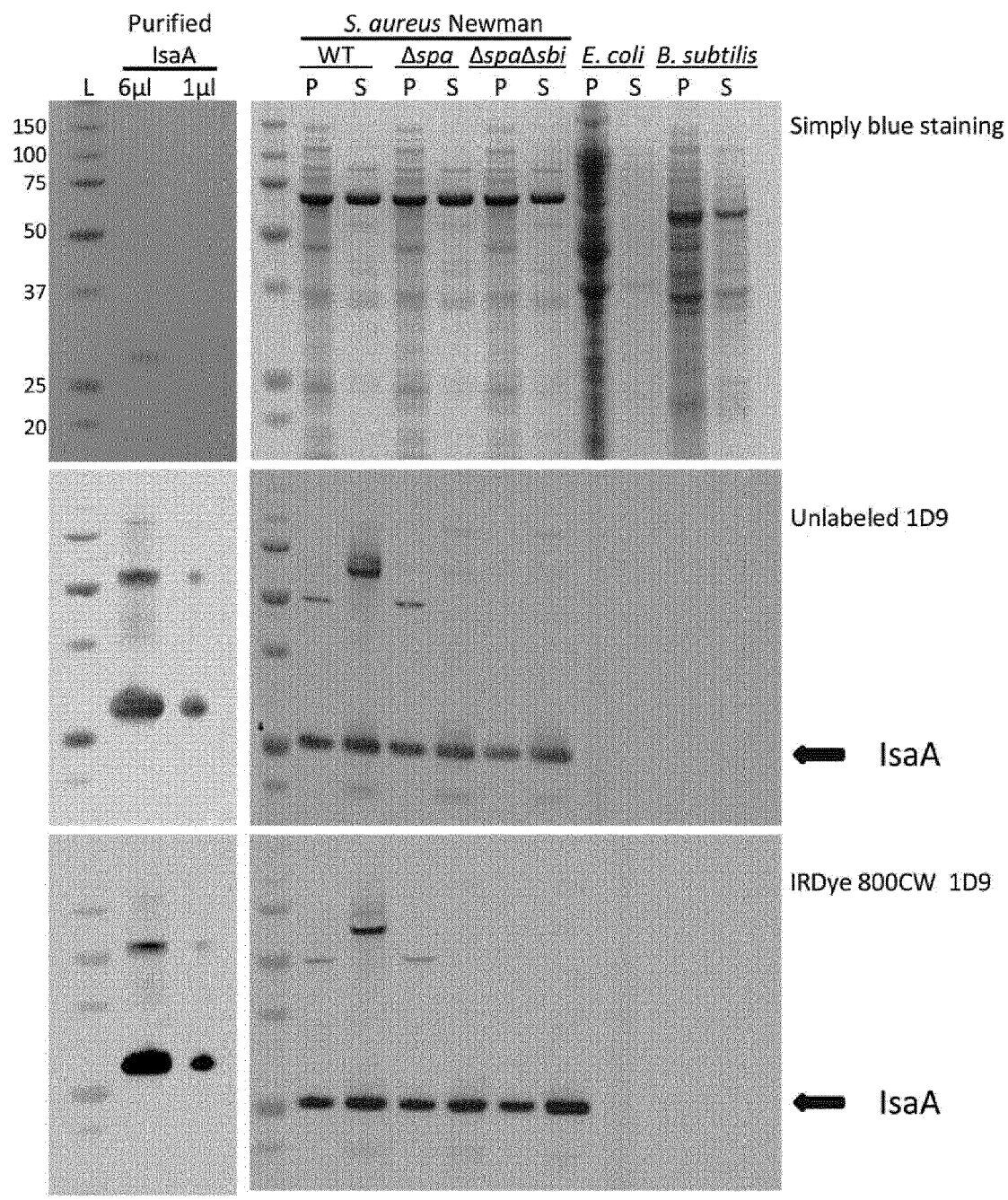

To confirm the functionality of the labeled 1D9 and to compare the IsaA antigen binding of labeled 1D9 to that of the unlabeled 1D9, replicate LDS-PAA gels were loaded with different amounts of isolated IsaA as well as cell pellet (P) and culture supernatant (S) fractions from the wild-type *S. aureus* strain Newman, as well as its derivatives lacking the sbi and/or spa genes (both encoding proteins that bind IgG). In addition, cell pellet and cultures supernatant fractions of the IsaA-negative control strains *Escherichia coli* (a Gram-negative bacterium) and *Bacillus subtilis* (a Gram-positive bacterium) were separated on the same gels. The results showed no differences in IsaA antigen binding for both the labeled and unlabeled 1D9 antibodies (FIG. 9C, compare middle and lower panels).

Labeled 1D9 Binds to *S. aureus* Cells and not to *E. coli* or *B. subtilis* Cells.

Figure 10A:
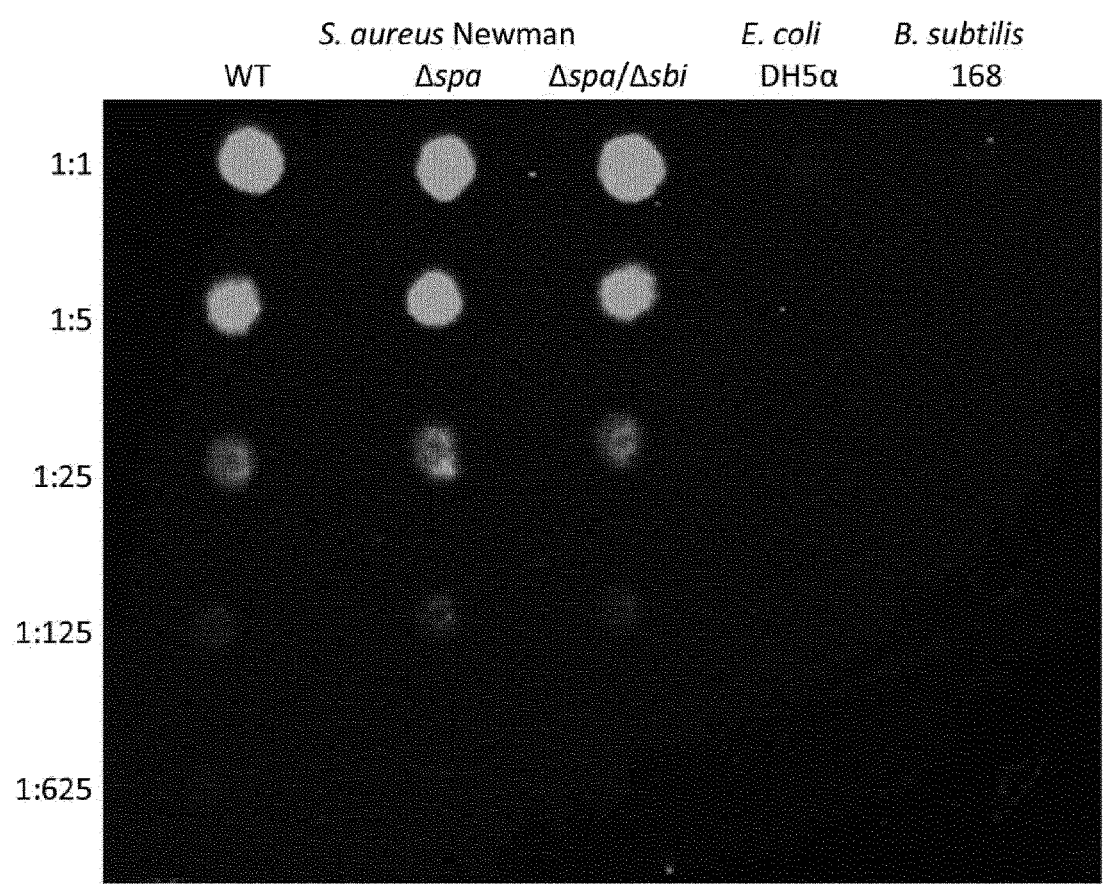
Figure 10B:
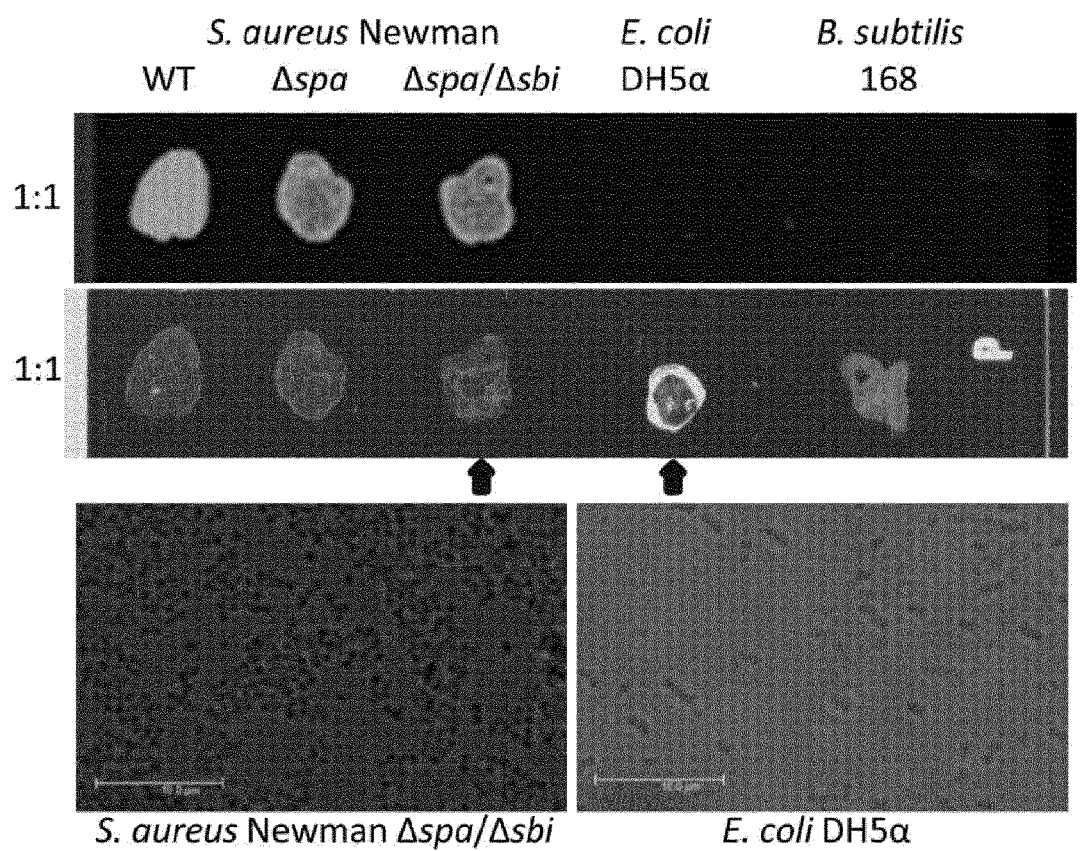

Overnight cultures of the wildtype *S. aureus* strain Newman and its spa and spa sbi mutant derivatives, along with overnight cultures of *E. coli* and *B. subtilis*, were incubated with the IRDye 800CW labeled HumAb 1D9 to allow its binding to cells. Next the cells were washed and spotted on a Whatman paper, which was scanned for fluorescence at 800 nm. The obtained images show bright fluorescence from the antibody bound to cells of the three *S. aureus* strains, while no signal was detectable for cells of *E. coli* or *B. subtilis* that had been incubated with the labeled antibody (FIG. 10A). Replacing the Whatman paper for glass slides produced similar results (FIG. 10B, upper panel) and allowed the visualization of the spotted cells (middle and lower panels).

Conclusion

The HumAb 1D9 retains its specificity for the IsaA protein of *S. aureus* upon conjugation to IRDye 800CW and the labeled HumAb 1D9 can be used for the specific detection of *S. aureus*. This implies that IRDye 800CW can be applied for diagnostic detection of *S. aureus* in vitro and probably also in vivo.

REFERENCES

1. Lowy F D. 1998. N Engl J Med 339:520-532.
2. Cosgrove S E. 2006. Clin Infect Dis 42 Suppl 2:S82-89.
3. Cosgrove S E et al. 2006 Infection control and hospital epidemiology: the official journal of the Society of Hospital Epidemiologists of America 26:166-174.
4. Noskin G A et al. 2005. The burden of *Staphylococcus aureus* infections on hospitals in the United States: an analysis of the 2000 and 2001 Nationwide Inpatient Sample Database. Arch Intern Med 165:1756-1761.
5. Chambers H F, Deleo F R. 2009. Nature reviews. Microbiology 7:629-641.
6. Verkaik N J et al. 2011. Immunotherapy 3:1063-1073.
7. Ziebandt A K et al. 2010. Proteomics 10:1634-1644.
8. Lorenz U et al. 2000. FEMS Immunol Med Microbiol 29:145-153.
9. Sakata N et al. 2005. Curr Microbiol 50:47-51.
10. Stapleton M R et al. 2007. J Bacteriol 189:7316-7325.
11. Dubrac S, Msadek T. 2004. J Bacteriol 186:1175-1181.
12. Dreisbach A et al. 2010. Proteomics 10:3082-3096.
13. Dreisbach A et al. 2011. Proteomics 11:3154-3168.
14. van der Kooi-Pol M M et al. 2012. J Invest Dermatol.
15. Lorenz U et al. 2011. Antimicrob Agents Chemother 55:165-173.
16. Sibbald M J et al. 2010. J Bacteriol 192:3788-3800.
17. Horsburgh M J et al. 2002. J Bacteriol 184:5457-5467.
18. Smith K et al. 2009. Nat Protoc 4:372-384.
19. Tiller T et al. 2008. J Immunol Methods 329:112-124.
20. Albrecht M T et al. 2007. Infect Immun 75:5425-5433.
21. McDougal L K et al. 2003. J Clin Microbiol 41:5113-5120.
22. Falugi F et al. 2013. MBio 4:e00575-00513.
23. von Kockritz-Blickwede M, Nizet V. 2009. J Mol Med (Berl) 87:775-783.
24. Pancari G et al. 2012. Front Cell Infect Microbiol 2:36.
25. DeJonge M et al. 2007. J Pediatr 151:260-265, 265 e261.
26. Weems J J, Jr. et al. 2006. Antimicrob Agents Chemother 50:2751-2755.
27. Benjamin D K et al. 2006. J Perinatol 26:290-295.
28. Rupp M E et al. 2007. Antimicrob Agents Chemother 51:4249-4254.
29. Ohlsen K, Lorenz U. 2010. Int J Med Microbiol 300:402-410.
30. Garcia-Lara J, Foster S J. 2009. Curr Opin Pharmacol 9:552-557.
31. van den Berg, S. et al. Int J Med Microbiol. 2014 Nov. 11. pii: 51438-4221(14)00150-7. doi: 10.1016/j.ijmm.2014.11.002. PMID: 25466204

The invention claimed is:

1. A method for in vitro detection of *Staphylococcus aureus*, comprising the steps of:
   (a) contacting a test sample with an isolated antibody or a functional fragment thereof, wherein the isolated antibody or functional fragment thereof binds to an epitope of Immunodominant Staphylococcal antigen A (IsaA), wherein said antibody or functional fragment thereof comprises the IsaA epitope-binding CDR sequences represented by SEQ ID NO: 1; SEQ ID NO: 2; SEQ ID NO: 3; SEQ ID NO: 4; SEQ ID NO: 5 and SEQ ID NO: 6, and
   (b) detecting formation of an antigen-antibody complex.

2. The method according to claim 1, wherein the isolated antibody or functional fragment thereof comprises a heavy chain comprising a sequence which is at least 85% identical to sequence of SEQ ID NO:13 and/or comprising a light chain sequence which is at least 85% identical to SEQ ID NO:14.

3. The method according to claim 1, wherein the isolated antibody or functional fragment thereof comprises at least one mutation in germ-line heavy-chain and/or kappa-chain sequence.

4. The method according to claim 1, wherein the isolated antibody or functional fragment thereof comprises a heavy chain sequence comprising a sequence of SEQ ID NO: 13 and a light chain sequence comprising a sequence of SEQ ID NO: 14.

5. The method according to claim 1, wherein the isolated antibody or functional fragment thereof is conjugated to a detectable label.

6. The method according to claim 1, wherein the isolated antibody or functional fragment thereof is conjugated to an infrared dye.

7. The method according to claim 1, wherein the isolated antibody or functional fragment thereof is conjugated to infrared dye 800CW.

8. The method according to claim 1, wherein the *Staphylococcus aureus* is a methicillin resistant *Staphylococcus aureus* (MRSA).

9. A method for detection of *Staphylococcus aureus*, comprising the steps of:
   (a) contacting a test sample with an isolated antibody or a functional fragment thereof, wherein the isolated antibody or functional fragment thereof binds to an epitope of Immunodominant Staphylococcal antigen A (IsaA), wherein said antibody or functional fragment thereof comprises the IsaA epitope-binding CDR sequences represented by SEQ ID NO: 1; SEQ ID NO: 2; SEQ ID NO: 3; SEQ ID NO: 4; SEQ ID NO: 5 and SEQ ID NO: 6, and
   (b) detecting formation of an antigen-antibody complex.

10. The method according to claim 9, wherein the isolated antibody or functional fragment thereof comprises a heavy chain comprising a sequence which is at least 85% identical to sequence of SEQ ID NO: 13 and/or comprising a light chain sequence which is at least 85% identical to SEQ ID NO: 14.

11. The method according to claim 9, wherein the isolated antibody or functional fragment thereof comprise at least one mutation in germ-line heavy-chain and/or kappa-chain sequence.

12. The method according to claim 9, wherein the isolated antibody or functional fragment thereof comprises a heavy chain sequence comprising a sequence of SEQ ID NO: 13 and a light chain sequence comprising a sequence of SEQ ID NO: 14.

13. The method according to claim 9, wherein the isolated antibody or functional fragment thereof is conjugated to a detectable label.

14. The method according to claim 9, wherein the isolated antibody or functional fragment thereof is conjugated to an infrared dye.

15. The method according to claim 9, wherein the isolated antibody or functional fragment thereof is conjugated to infrared dye 800CW.

16. The method according to claim 9, wherein the *Staphylococcus aureus* is a methicillin resistant *Staphylococcus aureus* (MRSA).

* * * * *